(12) United States Patent
Moss et al.

(10) Patent No.: US 8,828,380 B2
(45) Date of Patent: Sep. 9, 2014

(54) METHOD FOR THE TREATMENT OF PULMONARY DISEASE AND METHOD OF PRODUCING PROTEINS OF USE THEREIN

(75) Inventors: Joel Moss, Bethesda, MD (US); Linda Stevens, Gaithersburg, MD (US); Rodney L. Levine, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/394,393

(22) PCT Filed: Sep. 8, 2010

(86) PCT No.: PCT/US2010/048068
§ 371 (c)(1),
(2), (4) Date: Mar. 6, 2012

(87) PCT Pub. No.: WO2011/031713
PCT Pub. Date: Mar. 17, 2011

(65) Prior Publication Data
US 2012/0164123 A1     Jun. 28, 2012

Related U.S. Application Data

(60) Provisional application No. 61/241,311, filed on Sep. 10, 2009.

(51) Int. Cl.
*A61K 38/45*     (2006.01)
*A61K 38/17*     (2006.01)
*A61K 38/16*     (2006.01)

(52) U.S. Cl.
CPC ............. *A61K 38/17* (2013.01); *A61K 38/16* (2013.01)
USPC ........................................ 424/94.5; 435/68.1

(58) Field of Classification Search
CPC .............................. A61K 38/16; A61K 38/17
USPC ........................................ 424/94.5; 435/68.1
See application file for complete search history.

(56) References Cited

U.S. PATENT DOCUMENTS

2006/0036083 A1    2/2006  Moss et al.
2009/0203878 A1*   8/2009  Moss et al. ................... 530/324

FOREIGN PATENT DOCUMENTS

WO    WO 03/070176      8/2003
WO    WO 2004/003195    1/2004

OTHER PUBLICATIONS

Zou et al., Journal of Biological Chemistry, vol. 28, No. 27, p. 19653-19665, 2007.*
Girolamo et al. (FEBS Journal, vol. 272, p. 4565-4575, 2005).*
Adermann, "Defensins as Anti-Infective and Immunomodulatory Agents," *Expert. Opin. Ther. Patents*, vol. 16(9):1223-1234, 2006.
Corda et al., Mono-ADP-Ribosylation: A Tool for Modulating Immune Response and Cell Signaling, *Sci. STKE*, 2002(163):1-4, 2002.
Osago et al., "Precursor Ion Scanning and Sequencing of Arginine ADP-Ribosylated Peptide by Mass Spectrometry," *Anal. Biochem.*, Epub ahead of print, Jun. 26, 2009.
Paone et al., "ADP Ribosylation of Human Neutrophil Peptide-1 Regulates its Biological Properties," *Proc. Natl. Acad. Sci. USA*, vol. 99(12):8231-8235, 2002.
Paone et al., "ADP-Ribosyltransferase-Specific Modification of Human Neutrophil Peptide-1," *J. Biol. Chem.*, vol. 281(25):17054-17060, 2006.
Sell et al., "Conversion of Arginine into Ornithine by Advanced Glycation in Senescent Human Collagen and Lens Crystallins," *J. Biol. Chem.*, vol. 279(52):54173-54184, 2004.
Smith et al., "Sleep, psychological and clinical changes during alcohol withdrawal in NAD-treated alcoholics," *Quart. J. Stud. Alc.* vol. 32:982-994, 1971.
Zou et al., "Toward Understanding the Cationicity of Defensins: ARG and LYS Versus their Noncoded Analogs," *J. Biol. Chem.*, vol. 282(27):19653-19665, 2007.

* cited by examiner

*Primary Examiner* — Susan Hanley
*Assistant Examiner* — Damon B Bowe
(74) *Attorney, Agent, or Firm* — Klarquist Sparkman, LLP

(57) ABSTRACT

Disclosed herein are methods of treating a subject with pulmonary disease including administering to the subject a therapeutically effective amount of a polypeptide including at least one arginine residue susceptible to ADP-ribosylation and nicotinamide adenine dinucleotide (NAD). In some embodiments, the polypeptide and/or NAD is administered via inhalation. Also disclosed is a pharmaceutical composition including at least one polypeptide (such as HNP-1) and NAD. The disclosure also provides in vitro methods of producing a polypeptide with altered activity, including contacting the polypeptide with NAD and an arginine-specific mono-ADP-ribosyltransferase (for example, ART1) to produce a polypeptide including at least one ADP-ribosylated arginine residue, incubating the ADP-ribosylated polypeptide under conditions sufficient for conversion of at least one ADP-ribosylated arginine residue to ornithine, and isolating the ornithine-containing polypeptide. Methods of treating a subject with pulmonary disease including administering to the subject a therapeutically effective amount of a modified polypeptide (such as HNP-1) including at least one ornithine residue in place of an arginine residue are also disclosed.

10 Claims, 5 Drawing Sheets

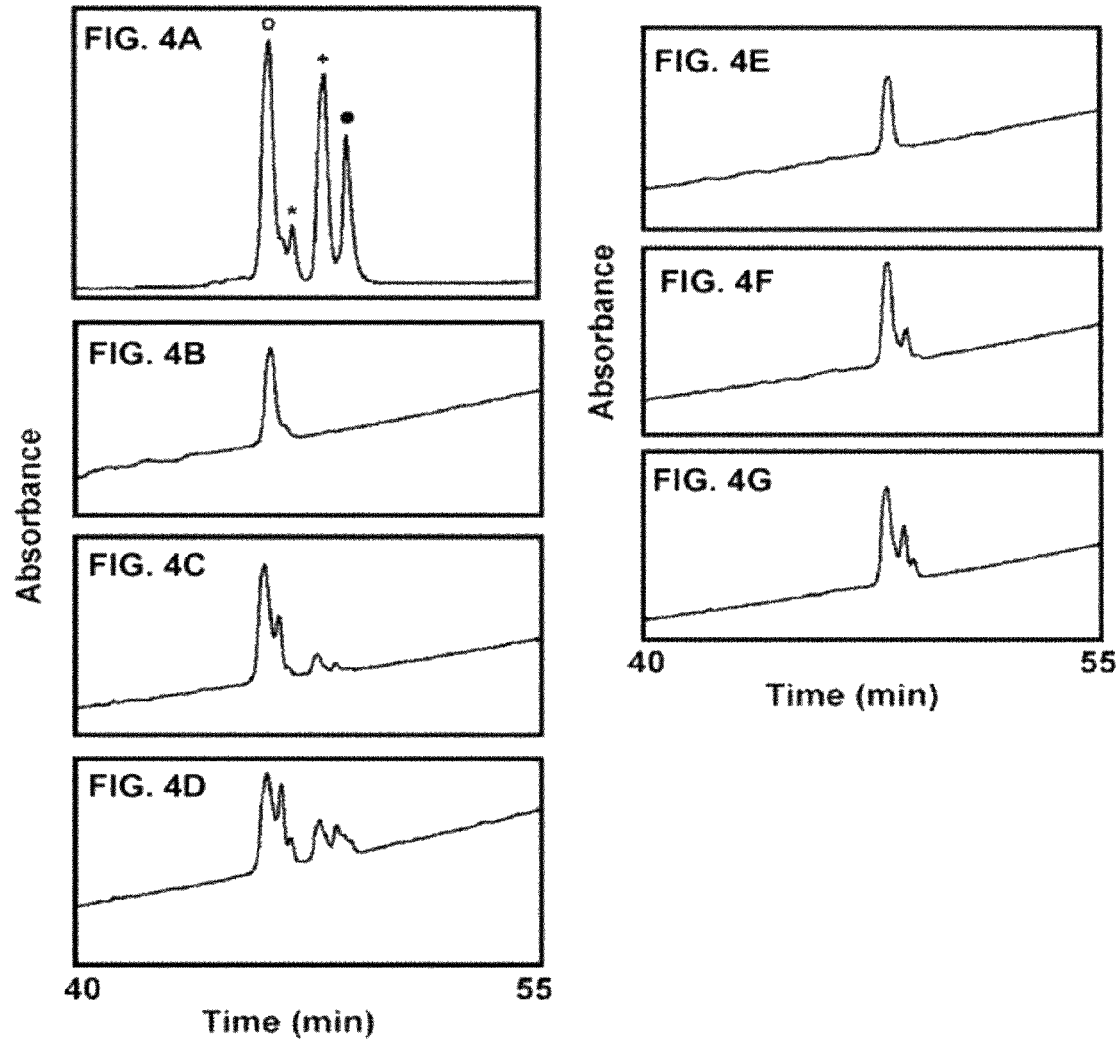

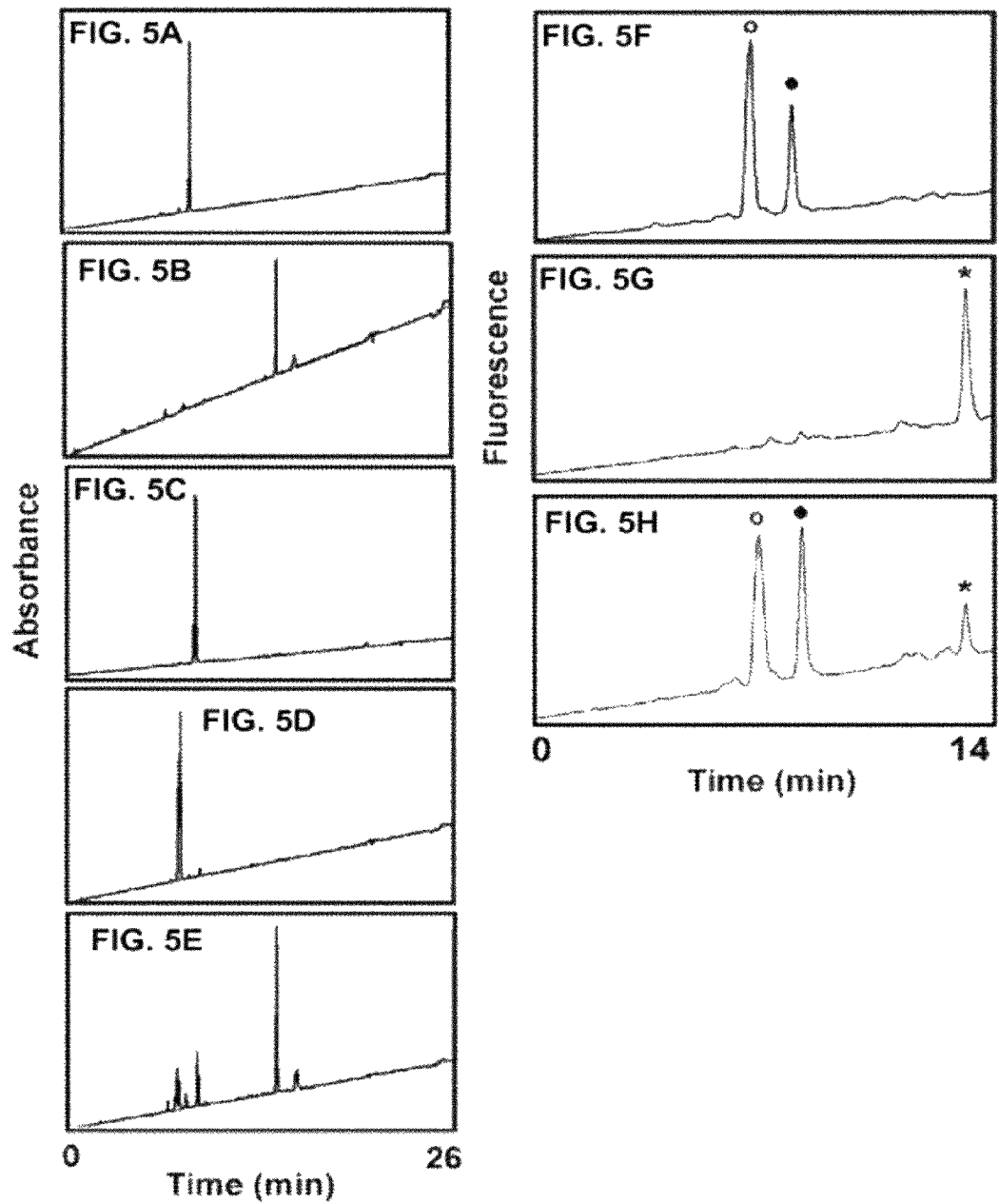

METHOD FOR THE TREATMENT OF PULMONARY DISEASE AND METHOD OF PRODUCING PROTEINS OF USE THEREIN

CROSS REFERENCE TO RELATED APPLICATIONS

This application is the U.S. National Stage of International Application No. PCT/US2010/048068, filed Sep. 8, 2010, which was published in English under PCT Article 21(2), which claims the benefit of U.S. Provisional Application No. 61/241,311, filed on Sep. 10, 2009, which is herein incorporated by reference in its entirety.

FIELD

This disclosure relates to methods of treating pulmonary disease, and in vitro methods of producing modified proteins, such as defensins, of use in treating pulmonary disease.

BACKGROUND

Mono-ADP-ribosylation is a post-translational modification of proteins in which the ADP-ribose moiety of nicotinamide adenine dinucleotide (NAD) is transferred to a specific amino acid. Several well-characterized mono-ADP-ribosyltransferases have been identified in viruses, bacteria and eukaryotes (Corda and DiGirolamo, *EMBO J.* 22:1953-1958, 2003). Arginine-specific mono-ADP-ribosyltransferase-1 (ART1) is present on the apical surface of epithelial cells in human airways and is linked to the cell surface by a glycosylphosphatidylinositol (GPI) anchor (Balducci et al., *Am. J. Respir. Cell. Mol. Biol.* 21:337-346, 1999; Okazaki and Moss, *J. Biol. Chem.* 273:23617-23620, 1998). ART1 modifies the arginines of several substrates, including defensins such as human neutrophil peptide (HNP)-1, thereby altering their activity (Corda and DiGirolamo *Sci. STKE* PE53, 2002; DiGirolamo et al., *FEBS J.* 272:4565-4575, 2005).

Neutrophils, a critical component of the innate immune system, are recruited to airways in response to inflammation or infection. Neutrophil defensins (HNP-1 to -3), stored in azurophilic granules, are small cationic peptides whose main function is to defend the lung against pathogenic micro-organisms (Bals and Hiemstra, *Eur. Respir. J.* 23:327-333, 2004). High levels of defensins have been found in patients with inflammatory lung diseases such as idiopathic pulmonary fibrosis (IPF) (Mukae et al., *Thorax* 57:623-628, 2002) and cystic fibrosis (Soong et al., *Inflamm. Res.* 46:98-102, 1997). In addition to antimicrobial activities and other diverse functions (Rehaume and Hancock, *Crit. Rev. Immunol.* 28:185-200, 2008), defensins interact with airway epithelial cells, increasing proliferation and stimulating wound repair (van Wetering et al., *J. Leukoc. Biol.* 77:444-450, 2005). HNPs 1-3 are arginine rich and differ in sequence by one amino acid. The arginines in HNP-1 are critical for maintaining activity of the protein (Zou et al, *J. Biol. Chem.* 282: 19653-19665, 2007).

In vitro, ART1 ADP-ribosylates HNP-1 on arginine 14 with a secondary site on arginine 24. Mono- and di-ADP-ribosylated HNP-1 have previously been isolated from the bronchoalveolar lavage fluid (BALF) of IPF and asthma patients, consistent with a role for the modified HNP-1 in disease (Paone et al., *J. Biol. Chem.* 281:17054-17060, 2006).

SUMMARY

There are a number of pulmonary diseases wherein therapeutic proteins are of use. This disclosure relates to polypeptides of use in treating those diseases. For example, defensins exhibit a wide range of antimicrobial and immune stimulatory activities, including cytotoxicity towards bacterial cells; however, these proteins are also cytotoxic for mammalian cells, including human epithelial and endothelial cells. This side effect may limit their usefulness for treating pulmonary disease. Thus, there exists a need to identify new methods of modifying existing agents, such as defensins, in order to modify their cytotoxic activity and potentially improve their effectiveness for treating pulmonary disease.

This disclosure provides methods of treating a subject with pulmonary disease including administering to the subject a therapeutically effective amount of a polypeptide including at least one arginine residue susceptible to ADP-ribosylation, and nicotinamide adenine dinucleotide (NAD). In particular examples, the polypeptide and/or NAD are administered by inhalation. In additional examples, the method further includes administering a therapeutically effective amount of an ART (such as an arginine-specific ART, for example mammalian ART1, ART2, or ART5). In some examples, the polypeptide is a defensin, for example, an alpha defensin, such as human neutrophil peptide-1 (HNP-1). Also disclosed is a pharmaceutical composition including at least one polypeptide (such as a defensin) and NAD.

The disclosure also provides in vitro methods of producing a polypeptide with altered activity, including contacting a polypeptide that includes at least one arginine residue susceptible to ADP-ribosylation with NAD and an arginine-specific mono-ADP-ribosyltransferase (for example, ART1) to produce a polypeptide including at least one ADP-ribosylated arginine residue. The methods include incubating the ADP-ribosylated polypeptide under conditions sufficient for conversion of at least one ADP-ribosylated arginine residue to ornithine, and isolating the ornithine-containing polypeptide. In particular examples, the conditions sufficient for conversion of ADP-ribosylated arginine to ornithine include incubation in a solution having a pH of about 7 to 9, incubation for a time of about 4 to 24 hours, and/or incubation at a temperature of about 30° C. to about 37° C. In some examples, the polypeptide is a defensin, such as an alpha defensin, such as HNP-1. Polypeptides made using these methods can be used in the therapeutic methods provided herein.

Also disclosed are methods of treating a subject with pulmonary disease, including administering to the subject a therapeutically effective amount of a modified polypeptide including at least one ornithine residue in place of an arginine residue. In particular examples, the modified polypeptide is a defensin, for example, an alpha defensin, such as HNP-1.

The foregoing and other features of the disclosure will become more apparent from the following detailed description, which proceeds with reference to the accompanying figures.

as ○, di-ADP-ribosylated-HNP-1; *, ADP-ribosyl-HNP-1-ornithine; +, mono-ADP-ribosylated-HNP-1; and ●, HNP-1. Data are representative of three experiments.

FIG. 2A is a chromatogram showing RP-HPLC separation of 1 nmol purified ADP-ribosyl-HNP-1-ornithine produced by incubating 10 nmol HNP-1 and 5 mM NAD with 12.8 nmol/h ART1 at 30° C. overnight, followed by acid hydrolysis. * indicates expected position of derivatized ornithine.

FIG. 2B is a chromatogram showing RP-HPLC separation of 3 nmol purified HNP-1 with 23 pmol ornithine added after hydrolysis. * indicates ornithine.

FIG. 2C is an RP-HPLC chromatogram of 3 nmol purified HNP-1.

FIG. 2D is a MS/MS profile of a tryptic digest of the ADP-ribosyl-HNP-1-ornithine from FIG. 2A. b8, HNP-1 amino acids 6 (Ile) through 13 (Glu); b9, HNP-1 amino acids 6 (Ile) through 14 (Arg converted to Orn).

FIG. 2E is a MS/MS profile of a tryptic digest of the HNP-1 from FIG. 2C. b8, HNP-1 amino acids 6 (Ile) through 13 (Glu); b9, HNP-1 amino acids 6 (Ile) through 14 (Arg).

Figure 3:
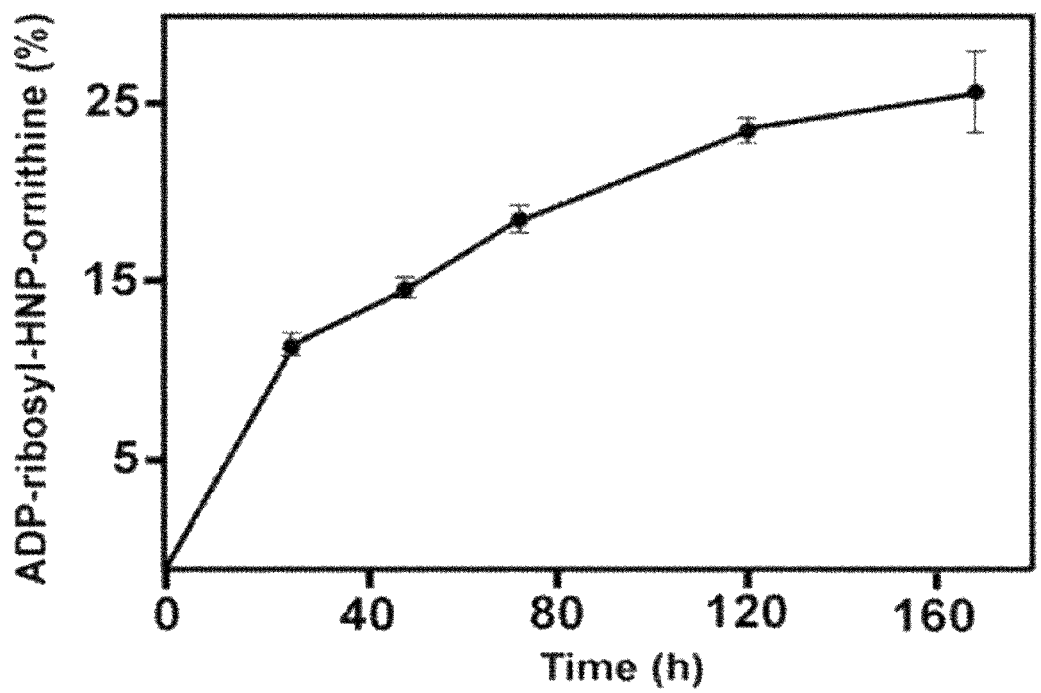

FIG. 3 is a graph showing percent of ADP-ribosyl-HNP-1-ornithine as a function of time in a reaction containing 3 nmol HNP-1, 5 mM NAD and 5.8 nmol/h ART1 at pH 7.5 and 30° C. ADP-ribosyl-HNP-1-ornithine was quantified as pmoles calculated from the area (mAu) under the peak identified as ADP-ribosyl-HNP-1-ornithine at 280 nm The reported percent was based on the total number of pmoles of reaction products in the separation. Data are mean±SD from four experiments.

FIG. 4A is an HPLC chromatogram of RP-HPLC separation of reaction products from overnight incubation of 10 nmol HNP-1 and 5 mM NAD with 12.8 nmol/h ART1 at 30° C. Peaks are identified as ○, di-ADP-ribosylated-HNP-1; *, ADP-ribosyl-HNP-1-ornithine; +, mono-ADP-ribosylated-HNP-1; and ●, HNP-1.

FIG. 4B is an HPLC chromatogram of purified di-ADP-ribosylated HNP-1 at pH 9 (time 0). Data is representative of three experiments.

FIG. 4C is an HPLC chromatogram of purified di-ADP-ribosylated HNP-1 incubated at pH 7 and 30° C. for 24 hours. Data is representative of two experiments.

FIG. 4D is an HPLC chromatogram of purified di-ADP-ribosylated HNP-1 incubated at pH 9 and 30° C. for 24 hours. Data is representative of three experiments.

FIG. 4E is an HPLC chromatogram of purified mono-ADP-ribosylated HNP-1 at pH 9 (time 0). Data is representative of three experiments.

FIG. 4F is an HPLC chromatogram of purified mono-ADP-ribosylated HNP-1 incubated at pH 7 and 30° C. for 24 hours. Data is representative of two experiments.

FIG. 4G is an HPLC chromatogram of purified mono-ADP-ribosylated HNP-1 incubated at pH 9 and 30° C. for 24 hours. Data is representative of three experiments.

FIG. 5A is an HPLC chromatogram of ADP-ribose and arginine incubated for 24 hours at 37° C. in 20 mM potassium phosphate, adjusted to pH 9 by NaOH.

FIG. 5B is an HPLC chromatogram of ornithine incubated for 24 hours at 37° C. in 20 mM potassium phosphate, adjusted to pH 9 by NaOH.

FIG. 5C is an HPLC chromatogram of ADP-ribosyl-[$^{14}$C]arginine incubated for 24 hours at 37° C. in 6 N HCl.

FIG. 5D is an HPLC chromatogram of ADP-ribosyl-[$^{14}$C]arginine at time 0.

FIG. 5E is an HPLC chromatogram of ADP-ribosyl-[$^{14}$C]arginine incubated for 24 hours at 37° C. in 20 mM potassium phosphate, adjusted to pH 9 by NaOH.

FIG. 5F is an amino acid analysis monitored by fluorescence of ADP-ribosyl-[$^{14}$C]arginine at time 0. ○, ADP-ribosyl-[$^{14}$C]arginine; ●, arginine.

FIG. 5G is an amino acid analysis monitored by fluorescence of ornithine (25 pmol). *, ornithine.

FIG. 5H is an amino acid analysis of ADP-ribosyl-[$^{14}$C] arginine incubated for 24 hours at 37° C. in 20 mM potassium phosphate, adjusted to pH 9 by NaOH. ○, ADP-ribosyl-[$^{14}$C]arginine; ●, arginine; *, ornithine.

SEQUENCE LISTING

The amino acid sequences listed in the accompanying sequence listing are shown using standard three letter code for amino acids, as defined in 37 C.F.R. 1.822.

The Sequence Listing is submitted as an ASCII text file, created on Mar. 5, 2012, 7.94 KB, which is incorporated by reference herein.

In the accompanying sequence listing:
SEQ ID NO: 1 is the amino acid sequence of the HNP-1 and HNP-2 prepro-protein.
SEQ ID NO: 2 is the amino acid sequence of HNP-1.
SEQ ID NO: 3 is the amino acid sequence of HNP-2.
SEQ ID NO: 4 is the amino acid sequence of the HNP-3 prepro-protein.
SEQ ID NO: 5 is the amino acid sequence of HNP-3.
SEQ ID NO: 6 is the amino acid sequence of the HNP-4 prepro-protein.
SEQ ID NO: 7 is the amino acid sequence of HNP-4.
SEQ ID NO: 8 is the amino acid sequence of the HD-5 prepro-protein.
SEQ ID NO: 9 is the amino acid sequence of HD-5.
SEQ ID NO: 10 is the amino acid sequence of the HD-6 prepro-protein.
SEQ ID NO: 11 is the amino acid sequence of HD-6.
SEQ ID NO: 12 is the amino acid sequence of the Def-X prepro-protein
SEQ ID NO: 13 is the amino acid sequence of Def-X.

DETAILED DESCRIPTION

Targeted ADP-ribosylation of specific arginines by ARTs, and their subsequent replacement with ornithine, is a novel alternative pathway for regulation of protein function through post-translational modification. Without being bound by theory, in addition to altering the molecular charge, secondary structure, and biological activity, the presence of ornithine at the position of one or more arginine residues and the absence of ADP-ribose would prevent a modified protein from interacting with ADP-ribosylacceptor hydrolases or serving as a target for subsequent ADP-ribosylation. ADP-ribosylacceptor hydrolases regulate cellular levels of ADP-ribosylated proteins. Moreover, the effects of ADP-ribosylation, such as on signal transduction by a polypeptide, would be altered.

Defensin polypeptides are antimicrobial peptides that are involved in the innate immune defense and are cytotoxic for microbes such as bacteria, fungi, and certain types of viruses. In addition, they stimulate IL-8 release from neighboring cells and induce an increase in T cell chemotaxis. The ADP-ribosylation of an arginine residue in an HNP-1 defensin polypeptide can alter its antimicrobial activity and/or modify an immune response (e.g., U.S. Pat. No. 7,511,015).

It is shown herein that ADP-ribosylated arginine residues in a polypeptide, such as a defensin polypeptide, are converted non-enzymatically to ornithine in vitro. Conversion of ADP-ribosylated arginine to ornithine also occurs in vivo, as demonstrated by the presence of HNP-1 containing both ADP-ribose and ornithine in bronchoalveolar lavage fluid from a patient with idiopathic pulmonary fibrosis.

Administering a polypeptide (such as a defensin) with at least one arginine susceptible to ADP-ribosylation and NAD to a subject (for example, by inhalation) provides the substrate and ADP-ribose source for production of ADP-ribosylated polypeptide because of the presence of ADP-ribosyltransferases on the surface of epithelial cells and inflammatory cells or secreted into the airway lumen. Subsequent conversion of the ADP-ribosylated arginine to ornithine can occur, which can be useful for treating pulmonary disease. Similarly, a polypeptide (such as a defensin) in which at least one arginine residue is replaced with an ornithine can be produced in vitro as described herein. The modified ornithine-containing polypeptide can be administered to a subject for treating pulmonary disease.

I. Abbreviations

ADP: adenosine diphosphate
ART1: arginine-specific mono-ADP-ribosyltransferase-1
BALF: bronchoalveolar lavage fluid
HNP: human neutrophil peptide
HPLC: high-performance liquid chromatography
IPF: idiopathic pulmonary fibrosis
MS: mass spectrometry
NAD: nicotinamide adenine dinucleotide
OPA: o-phthalaldehyde
Orn: ornithine
RP-HPLC: reverse phase high-performance liquid chromatography II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank Accession numbers mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Administration: Administration of an active compound ("agent") or composition (such as those peptides provided herein) can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

ADP-ribosylation: Reaction in which ADP-ribose is covalently attached to another compound. A family of eukaryotic and prokaryotic mono-ADP-ribosyltransferases (ARTs) catalyze the transfer of ADP-ribose from nicotinamide adenine dinucleotide (NAD) to proteins.

As disclosed herein, a number of proteins used in host defense are basic and arginine-rich and thus could serve as acceptors for ADP-ribose. These include, but may not be limited to, alpha defensins (HNP-1, HNP-2, HNP-3, HNP-4, HD-5, HD-6); beta defensins (hBD1, hBD-2, hBD-3, hBD-4); Major Basic Protein; Eosinophil Cationic Protein; cathelicidin antimicrobial peptide (e.g., hCAP18) and lysozyme.

Altered activity: As used herein, an ornithine-containing polypeptide with "altered activity" refers to any polypeptide with at least one ornithine residue that exhibits a change in its ability to interact with another molecule (such as an increase or decrease in binding affinity to another molecule) or exhibits a change (such as an increase or decrease) in one or more functions or biological activities of the protein. In some examples, when the ornithine-containing polypeptide is a defensin, an altered activity can be a change in the polypeptide's antimicrobial activity. An alteration in antimicrobial activity can include, for example, an increase in cytokine production or an increase in recruitment of inflammatory cells, as discussed in greater detail in the sections below.

Arginine: An amino acid ($C_6H_{14}N_4O_2$) found in plants and animals that is essential for the human diet; also produced by the breakdown of proteins. Also encompassed are functional analogues of arginine, and structurally modified arginine molecules (e.g., agmatine).

Defensins: Small, cationic peptides that have six conserved cysteine residues that form three disulfide bonds. Functional defensins arise by the sequential post-translational processing of a prepro-protein of 93-95 amino acids in length. The members of the defensin family are divided into different classes. The alpha-defensins generally contain 29-33 residues. The beta-defensins are more basic than alpha defensins and are generally between 34-37 amino acids in length. See, e.g., Raj et al., *Biochem J.;* 347:633-41, 2000. The recently identified theta defensins are formed by the head-to-tail linkage of two alpha defensin-related nonapeptides, generating a circular 18-residue polypeptide (Tang et al., *Science;* 286: 498-502, 1999).

Defensins were first identified in neutrophils and have been detected in human, rabbit, guinea pig, and rat phagocytes. Alpha defensins include, but are not limited to, HNP-1, HNP-2, HNP-3, HNP-4, human defensin (HD)-5, and HD-6. Alpha defensins also include the recently identified HNP-4 homolog, defensin (Def)-X (see U.S. Pat. No. 6,329,340).

HNP-1 and HNP-2 are products of the same gene (GenBank Accession No. NP_004075 herein incorporated by reference as present in GenBank on Sep. 10, 2009). HNP-3 differs from HNP-1 by only one amino acid, but is the product of a different prepro-protein (GenBank Accession No. NP_005208, herein incorporated by reference as present in GenBank on Sep. 10, 2009). HNP-4 is the product of a different gene (GenBank Accession No. NP_001916 herein incorporated by reference as present in GenBank on Sep. 10, 2009). HD-5 (GenBank Accession No. NP_066290) and HD-6 (GenBank Accession No. NP_001917), each herein incorporated by reference as present in GenBank on Sep. 10, 2009, are two human enteric defensins.

Defensins are toxic for a variety of infectious agents, such as Gram-negative bacteria, Gram-positive bacteria, fungi, and certain enveloped viruses. Defensins act by forming pores in membranes of the infectious agent and generating voltage-dependent channels. Antimicrobial activities of defensins include, but are not limited to, lysis of bacteria, fungi, or viruses; toxicity for bacteria, fungi or viruses; leukocyte (e.g., T cell) chemotaxis; and leukocyte (e.g., neutrophil) recruitment. Without being bound by theory, defensins play an important role in the body's natural immunity against infections. Defensins are also cytotoxic for several normal and malignant cells. A "modified defensin" is a defensin that includes at least one modified arginine residue (such as an ADP-ribosylated arginine) or a defensin that contains at least one ornithine residue in place of an arginine residue. An "unmodified defensin" is a defensin that includes only unmodified (native) arginine residues.

Isolated: A biological component (such as a nucleic acid, peptide or protein) that has been substantially separated, produced apart from, or purified away from other biological components in the cell of the organism in which the component naturally occurs, e.g., other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell, as well as chemically synthesized nucleic acids and proteins.

Mono-ADP-ribosyltransferase (ART): A family of enzymes that catalyze the transfer of ADP-ribose from NAD to proteins. Mammalian ARTs that are secreted or localized on the cell surface through glycosylphosphatidylinositol (GPI) anchors are expressed preferentially by epithelial and inflammatory cells such as lymphocytes and neutrophils. Substrates of the five known mammalian ADP-ribosyltransferases (ART1, ART2, ART3, ART4, and ART5) include proteins that are involved in critical cellular events (e.g., lymphocyte activation, neutrophil chemotaxis). Three of these transferases, ART1, ART2, and ART5, specifically modify arginine residues in proteins.

Bacterial products (e.g., cholera toxin, pertussis toxin, and diphtheria toxin) are also included among the ARTs.

Nicotinamide adenine dinucleotide (NAD): A dinucleotide compound containing an adenine base and a nicotinamide joined through their phosphate groups having the structure:

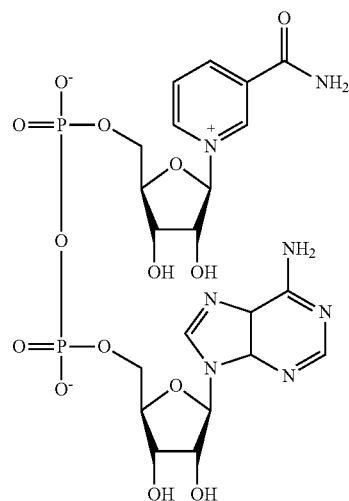

NAD is an essential enzyme cofactor in metabolism. For example, it acts as a coenzyme in redox reactions, providing transfer of electrons from one redox reaction to another. It also serves as a donor of ADP-ribose groups in ADP-ribosylation reactions and as a precursor of the second messenger molecule cyclic ADP-ribose.

Ornithine: An amino acid ($C_5H_{12}N_2O_2$) which is part of the urea cycle having the structure:

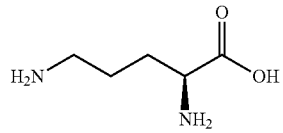

Ornithine and urea are produced by the hydrolysis of arginine, which is catalyzed by arginase. Ornithine may also be produced non-enzymatically from ADP-ribosylated arginine. Ornithine is not coded for by DNA, and is therefore not incorporated into naturally occurring primary amino acid sequences.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as ADP-ribosylated proteins, ribosyl-proteins, ornithine-containing proteins, and glycoproteins. The term polypeptide is specifically intended to cover naturally occurring proteins, as well as those that are recombinantly or synthetically produced.

Polypeptides (such as those provided herein) may include one or more conservative amino acid substitutions. Conservative substitutions are the substitution of an amino acid residue for another amino acid residue having similar biochemical properties. Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 1-10 conservative substitutions, 2-5 conservative substitutions, or 4-9 conservative substitutions.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Any polypeptide sequence variant will preferably introduce no more than twenty, and preferably fewer than ten amino acid substitutions (for example, conservative substitutions) into the encoded polypeptide. Thus, the disclosed peptide, such as the disclosed defensins, can have 1-10, 1-5, or 1, 2, 3, 4, or 5 conservative amino acid substitutions shown above. Variant amino acid sequences may, for example, be 80%, 90%, 95%, 98%, 99%, or more identical to the native amino acid sequence. Programs and algorithms for determining percentage identity can be found at the NCBI website.

Pharmaceutical agent or composition: A chemical compound or composition capable of inducing a desired therapeutic or prophylactic effect when properly administered to a subject or a cell.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of compounds, such as peptides or modified peptides, such as alpha defensins or modified alpha defensins.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate.

Pulmonary disease: A disease of the respiratory system, including the lungs and bronchial tree. Pulmonary diseases include, for example, cystic fibrosis, emphysema, asthma, sarcoidosis, chronic bronchitis, bronchopulmonary dysplasia, pulmonary fibrosis, pneumonia, and adult respiratory distress syndrome.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Substantially purified polypeptide as used herein refers to a polypeptide (such as a defensin polypeptide, for example a modified defensin polypeptide) that is substantially free of other proteins, lipids, carbohydrates or other materials with which it is naturally associated. In one embodiment, the polypeptide is at least 50%, for example at least 80%, free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Recombinant: A recombinant nucleic acid or protein is one that has a sequence that is not naturally occurring or was made artificially. Artificial combination is often accomplished by chemical synthesis or, more commonly, by the artificial manipulation of isolated segments of nucleic acids, e.g., by genetic engineering techniques. In some cases, a recombinant protein is one encoded by a recombinant nucleic acid molecule.

Subject: Living multi-cellular vertebrate organisms, a category that includes both human and non-human mammals. Includes subjects that have or may be susceptible to pulmonary disease.

Susceptible to ADP-ribosylation: A molecule (for example an amino acid residue, such as an arginine residue) that can be modified by an ADP-ribose (is available for ADP-ribosylation). ADP-ribosylation of a molecule (such as an arginine residue) can be determined by one of skill in the art for example, using the methods described herein, such as HPLC or MS methods. Such methods can identify which residue(s) include the ADP-ribose modification, thus identifying the residue(s) that are susceptible to ADP-ribosylation. In a particular example, the amino acid arginine (either isolated arginine, or arginine present in a polypeptide or protein, such as a defensin) can be modified by an ADP-ribose, for example, by transfer of an ADP-ribose to arginine to produce ADP-ribosyl-arginine, such as by an ADP-ribosyltransferase.

Therapeutically effective amount: An amount or dose sufficient to prevent advancement, or to cause regression of a disease (such as pulmonary disease, for example, cystic fibrosis, emphysema, asthma, sarcoidosis, chronic bronchitis, bronchopulmonary dysplasia, pulmonary fibrosis, pneumonia, or adult respiratory distress syndrome), or which is capable of relieving symptoms caused by the disease.

Treatment: Refers to both prophylactic inhibition of initial infection or disease, and therapeutic interventions to alter the natural course of an untreated infection or disease process, such as a pulmonary disease.

III. Methods of Treating Pulmonary Disease

Disclosed herein are methods of treating a subject with pulmonary disease. In some examples, the method includes administering to the subject a therapeutically effective amount of a polypeptide with at least one arginine residue susceptible to ADP-ribosylation and NAD. In some embodiments, the polypeptide and/or NAD are administered by inhalation. In some examples, the polypeptide is susceptible to ADP-ribosylation on more than one arginine residue simultaneously such as, at least two, at least three, at least four, or more arginine residues. In additional examples, the method also includes administering a therapeutically effective amount of an ART (such as ART1) to the subject.

In some examples, the polypeptide includes an enzyme, a cytokine, a chemokine, an anti-inflammatory peptide, a receptor ligand, a hormone, an antigen, or an antibody. In particular examples, the polypeptide is a defensin, such as an alpha defensin polypeptide (for example a mammalian alpha defensin, such as a human, monkey, rabbit, rat, cat, dog, pig, sheep, or mouse alpha defensin). In a specific, non-limiting example, the alpha defensin is human neutrophil peptide (HNP)-1. In other specific, non-limiting examples, the alpha defensin polypeptide is HNP-2, HNP-3, HNP-4, HD-5, HD-6, or Def-X.

The alpha defensins include HNP-1, HNP-2, HNP-3, HNP-4, HD-5, HD-6, and Def-X. HNP-1 and HNP-2 are products of the same 94 amino acid prepro-protein. In one embodiment, this protein has the following sequence:
MRTLAILAAILLVALQAQAEPLQA-RADEVAAAPEQIAADIPEVVVSL AWDESLAPKH-PGSRKNMACYCRIPACIAGER-RYGTCIYQGRLWAFC C; (SEQ ID NO: 1, see also GenBank Accession No. NP_004075, herein incorporated by reference as present in GenBank on Sep. 10, 2009).

HNP-1 is one member of the family of alpha defensins produced by cleavage of the prepro-protein. In one embodiment, HNP-1 has a sequence as set forth as:

(SEQ ID NO: 2)
ACYCRIPACIAGERRYGTCIYQGRLWAFCC;.

HNP-2 is another member of the family of alpha defensins produced by cleavage of the prepro-protein. In one embodiment, HNP-2 has a sequence as set forth as:

(SEQ ID NO: 3)
CYCRIPACIAGERRYGTCIYQGRLWAFCC;.

HNP-3 is a third member of the family of alpha defensins produced by cleavage of a prepro-protein. In one embodiment, the HNP-3 prepro-protein has a sequence set forth as:
MRTLAILAAILLVALQAQAEPLQA-RADEVAAAPEQIAADIPEVVVSL AWDESLAPKH-PGSRKNMDCYCRIPACIAGER-RYGTCIYQGRLWAFC C (SEQ ID NO: 4, see also, GenBank Accession No. NP_005208, herein incorporated by reference as present in GenBank on Sep. 10, 2009).

In one embodiment, HNP-3 has a sequence as set forth as:

(SEQ ID NO: 5)
DCYCRIPACIAGERRYGTCIYQGRLWAFCC;.

HNP-4 is an alpha defensin that is the product of a prepro-protein having a sequence as set forth as:
MRIIALLAAILLVALQVRAG-PLQARGDEAPGQEQRGPEDQDISISFAW DKSSALQVSGSTRGMVCSCRLVFCR-RTELRVGNCLIGGVSFTYCCTR VD (SEQ ID NO: 6, see also GenBank Accession No. NP_001916, herein incorporated by reference as present in GenBank on Sep. 10, 2009).

In one embodiment, HNP-4 has a sequence as set forth as:

(SEQ ID NO: 7)
VCSCRLVFCRRTELRVGNCLIGGVSFTYCCTRVD;.

HD-5 is produced by cleavage of the following prepro-protein having a sequence as set forth as:
MRTIAILAAILLVALQAQAESLQERADE-ATTQKQSGEDNQDLAISFA GNGLSALRTSG-SQARATCYCRTGRCATRESLSGVCEIS-GRLYRLCCR; (SEQ ID NO: 8, GenBank Accession No. NP_066290, herein incorporated by reference as present in GenBank on Sep. 10, 2009).

In one embodiment, HD-5 has a sequence as set forth as:

(SEQ ID NO: 9)
ATCYCRTGRCATRESLSGVCEISGRLYRLCCR;.

HD-6 is produced by cleavage of the following prepro-protein having a sequence as set forth as:
MRTLTILTAVLLVALQAKAEPLQAED-DPLQAKAYEADAQEQRGAND QDFAVSFAE-DASSSLRALGSTRAFTCHCRRSCYSTEY-SYGTCTVMGI NHRFCCL; (SEQ ID NO: 10, GenBank Accession No. NP_001917, herein incorporated by reference as present in GenBank on Sep. 10, 2009).

In one embodiment, HD-6 has a sequence as set forth as:

(SEQ ID NO: 11)
TCHCRRSCYSTEYSYGTCTVMGINHRFCCL;.

Def-X is produced by cleavage of the following prepro-protein having a sequence as set forth as:
MRTLTLLSAFLLVALQAWAEPLQARA-HEMPAQKQPPADDQDVVIYF SGDDSCSLQVPG-STKGLICHCRVLYCIFGEHLGGTC-FILGERYPICCY (SEQ ID NO: 12, see U.S. Pat. No. 6,329,340).

In one embodiment, Def-X has a sequence as set forth as:

(SEQ ID NO: 13)
ICHCRVLYCIFGEHLGGTCFILGERYPICCY.

In particular examples, the defensin is HNP-1 (for example, SEQ ID NO: 2). In some examples, HNP-1 is susceptible to ADP-ribosylation on an arginine residue at position 14 of SEQ ID NO: 2. In other examples, HNP-1 is susceptible to ADP-ribosylation on an arginine residue at position 24 of SEQ ID NO: 2. In some examples, HNP-1 is susceptible to ADP-ribosylation on more than one arginine residue simultaneously such as, at least two, at least three, or at least four arginine residues. In a particular example, HNP-1 is susceptible to ADP-ribosylation on arginines at both position 14 and position 24 of SEQ ID NO: 2.

The disclosed methods include administering a therapeutically effective amount of a polypeptide including at least one arginine residue susceptible to ADP-ribosylation to a subject. An arginine residue susceptible to ADP-ribosylation is an arginine residue (for example, an arginine residue in a polypeptide) that can be modified by an ADP-ribose (is available for ADP-ribosylation), for example, by transfer of an ADP-ribose to the arginine residue by an ART. ADP-ribosylation of an arginine residue can be determined by one of skill in the art for example, using the methods described herein, such as HPLC or MS methods. Such methods can identify which arginine residue(s) include the ADP-ribose modification, thus identifying the residue(s) that are susceptible to ADP-ribosylation.

A therapeutically effective amount of a polypeptide can be the amount of the polypeptide necessary to treat a pulmonary disease of the subject in conjunction with administration of NAD, for example, by increasing ADP-ribosylation of the polypeptide and its subsequent conversion to a polypeptide containing at least one ornithine residue in place of an arginine residue. In some examples, the polypeptide can be administered in dosages from about 1 μg/kg body weight to about 100 mg/kg body weight (such as about 1 μg/kg to 1 mg/kg or about 10 μg/kg to 10 mg/kg). The provided amounts are exemplary doses; one of skill in the art can readily determine suitable dosages. In some examples, the polypeptide is administered to the subject via inhalation.

In particular examples, the polypeptide is a defensin, such as an alpha defensin, for example, HNP-1. In some examples, HNP-1 is administered to a subject with pulmonary disease in dosages from about 1 μg/kg body weight to about 100 mg/kg body weight (such as about 1 μg/kg to 1 mg/kg or about 10 μg/kg to 10 mg/kg).

The disclosed methods also include administering a therapeutically effective amount of NAD to the subject via inhalation. NAD serves as a source of ADP-ribose, which can be transferred to a polypeptide (such as a defensin, for example, HNP-1) by an ART, which may be present in the airway on epithelial cells or on inflammatory cells recruited to the lung in a disease state. A therapeutically effective amount of NAD can be the amount of NAD necessary to treat a pulmonary disease of a subject, for example, by increasing ADP-ribosylation of a defensin polypeptide and its subsequent conversion to a defensin containing at least one ornithine residue in place of an arginine residue. In some examples, the amount of NAD may be about 0.5 μM to 20 mM achieved surface concentration (for example, about 5 μM to about 2 mM, about 25 μM to about 1 mM, or about 50 μM to about 200 μM achieved surface concentration of NAD). An "achieved surface concentration" is the concentration of a particular compound, such as NAD, that is achieved, or present, at the surface of a cell or tissue, for example, at the surface of lung epithelial lining The provided amounts are exemplary doses; one of skill in the art can readily determine suitable dosages.

In some examples, the method further includes administering a therapeutically effective amount of an ART polypeptide to the subject in addition to the polypeptide (for example, a defensin, such as HNP-1) and NAD. In some examples, the ART is ART1, ART2, or ART5. In a particular example, the ART is ART1. A therapeutically effective amount can be the amount of ART polypeptide necessary to treat a pulmonary disease of the subject in conjunction with administration of a polypeptide (such as a defensin, for example, HNP-1) and NAD, for example, by increasing ADP-ribosylation of the polypeptide and its subsequent conversion to a polypeptide containing at least one ornithine residue in place of an arginine residue. In some examples, the ART polypeptide can be administered in dosages from about 1 μg/kg body weight to about 100 mg/kg body weight (such as about 1 μg/kg to 1 mg/kg or about 10 μg/kg to 10 mg/kg). The provided amounts are exemplary doses; one of skill in the art can readily determine suitable dosages.

Also disclosed herein is a method of treating a subject with pulmonary disease including administering a therapeutically effective amount of a modified polypeptide, wherein the modified polypeptide includes at least one ornithine residue in place of an arginine residue (such as a modified polypeptide including at least one ornithine residue produced in vitro as described in Section IV, below). In some examples, the modified polypeptide includes a modified enzyme, cytokine, chemokine, anti-inflammatory peptide, receptor ligand, hormone, antigen, or antibody. In a particular example, the modified polypeptide is a modified defensin. In some examples, the modified polypeptide includes more than one ornithine residue in place of an arginine residue, such as at least two, at least three, at least four, or more ornithine residues.

A therapeutically effective amount of a modified polypeptide including at least one ornithine residue in place of an arginine residue can be the amount necessary to treat a pulmonary disease of the subject. In some examples, the modified polypeptide can be administered in dosages from about 1 μg/kg body weight to about 100 mg/kg body weight (such as about 1 μg/kg to 1 mg/kg or about 10 μg/kg to 10 mg/kg). The provided amounts are exemplary doses; one of skill in the art can readily determine suitable dosages.

In particular examples, the modified polypeptide is a modified defensin polypeptide, such as a modified HNP-1 polypeptide. In particular, non-limiting examples, the modified defensin polypeptide is an HNP-1 polypeptide including an ornithine residue at position 14 of HNP-1 (for example, position 14 of SEQ ID NO: 2), an HNP-1 polypeptide including an ornithine residue at position 24 of HNP-1 (for example, position 24 of SEQ ID NO: 2), or an HNP-1 polypeptide including an ornithine residue at positions 14 and 24 of HNP-1 (for example, positions 14 and 24 of SEQ ID NO: 2). In some examples, the modified HNP-1 polypeptide can be administered in dosages from about 1 μg/kg body weight to about 100 mg/kg body weight (such as about 1 μg/kg to 1 mg/kg or about 10 μg/kg to 10 mg/kg).

The disclosed methods include treating a subject with pulmonary disease, including, but not limited to, cystic fibrosis, emphysema, asthma, sarcoidosis, chronic bronchitis, bronchopulmonary dysplasia, pulmonary fibrosis, pneumonia, and adult respiratory distress syndrome. The subject can be any mammal. In one example, the subject is human. In other examples, the subject may be a monkey, rabbit, rat, mouse, pig, sheep, dog, or cat.

Cystic fibrosis is a recessive genetic disease in which the exocrine glands of afflicted individuals produce abnormally thick mucus which block the intestines and lung passageways and produce scarring and lesions in the lungs and pancreas.

Emphysema is condition in which there is over-inflation of structures in the lungs known as alveoli, or air sacs. This over-inflation results from a breakdown of the walls of the alveoli, which causes a decrease in respiratory function and often, breathlessness. Early symptoms of emphysema include shortness of breath and cough. Emphysema (together with chronic bronchitis) is considered chronic obstructive pulmonary disease (COPD).

Asthma is a disorder of the respiratory system characterized by inflammation, narrowing of the airways and increased reactivity of the airways to inhaled agents. Asthma is frequently, although not exclusively, associated with atopic or allergic symptoms.

Sarcoidosis is a disease of unknown cause in which inflammation, consisting of granulomas (clusters of macrophages, lymphocytes, and multinucleated giant cells), occurs in lymph nodes, lungs, liver, eyes, skin, or other tissues. Possible causes of sarcoidosis include a hypersensitivity response, a genetic predisposition, infection, or chemicals.

Chronic bronchitis is an inflammation of the lining of the bronchial tubes. When the bronchi are inflamed and/or infected, less air is able to flow to and from the lungs and a heavy mucus or phlegm is coughed up, resulting in bronchitis. A brief attack of acute bronchitis with cough and mucus production can occur with severe colds. Chronic bronchitis is characterized by the presence of a mucus-producing cough most days of the month, three months of a year for two successive years without other underlying disease to explain the cough. It may precede or accompany pulmonary emphysema. Cigarette smoking is by far the most common cause of chronic bronchitis. The bronchial tubes of people with chronic bronchitis may also have been irritated initially by bacterial or viral infections. Air pollution and industrial dusts and fumes are also causes. Once the bronchial tubes have been irritated over a long period of time, excessive mucus is produced constantly, the lining of the bronchial tubes becomes thickened, an irritating cough develops, air flow may be hampered, and the lungs are endangered. The bronchial tubes then make an ideal breeding place for infectious agents. Chronic bronchitis (together with emphysema) is considered to be COPD.

Bronchopulmonary dysplasia (BPD) is a chronic lung disorder that is most common among children who were born prematurely, with low birth weight and who received prolonged mechanical ventilation to treat respiratory distress syndrome. BPD is clinically defined as oxygen dependence to 21 post-natal days. BPD is characterized by inflammation and scarring in the lungs. More specifically, the high pressures of oxygen delivery result in necrotizing bronchiolitis and alveolar septal injury, further compromising oxygenation of blood. With the advent of surfactant therapy and high frequency nasal ventilation and oxygen supplementation, infants with BPD experience much milder injury without necrotizing bronchiolitis or alveolar septal fibrosis. Instead, there usually are uniformly dilated acini with thin alveolar septa and little or no interstitial fibrosis.

Pulmonary fibrosis (or idiopathic pulmonary fibrosis, IPF) is a chronic inflammation and progressive fibrosis of alveolar walls, with steady, progressive shortness of breath, resulting in death from lack of oxygen or right heart failure. The word "idiopathic" is used to describe the disease because the cause of IPF is unknown. Currently, it is believed that IPF may result from either an autoimmune disorder or the after effects of an infection, most likely a virus.

Pneumonia is an inflammation of the lungs caused by a bacterial, viral, or fungal infection for example, *Pneumococcus, Streptococcus, Hemolyticus, Staphylococcus*, Friedländer's bacillus (*Klebsiella pneumonia*), and influenza bacillus. Symptoms include high fever, chest pain, difficulty breathing, coughing and sputum.

Adult respiratory distress syndrome (ARDS) is a sudden pulmonary interstitial and alveolar edema, which usually develops within a few days after an initiating trauma. ARDS is thought to result from alveolar injury that has led to increased capillary permeability. It is also sometimes called acute respiratory distress syndrome.

The effectiveness of treatment of a subject with a pulmonary disease with a polypeptide and NAD (administered with or without an ART), or with a modified polypeptide containing at least one ornithine residue, can be measured by assessing the signs and symptoms of the disease (for example, frequency or severity of symptoms) and monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. An increase (such as a statistically significant increase), as determined by mathematical formulas well known to those skilled in the art, in one or more of these parameters indicates efficacy of the treatment with the polypeptide and NAD (administered with or without an ART) or the modified polypeptide containing at least one ornithine residue.

The methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expiratory volume (FEV 1), allows bronchoconstriction to be quantitatively evaluated. An increase (such as a statistically significant increase), as determined by mathematical formulas well known to those skilled in the art, in FVC or FEV1 reflects a decrease in bronchoconstriction, and indicates that the polypeptide and NAD therapy (administered with or without an ART), or therapy with the modified polypeptide containing at least one ornithine residue is effective (for example an increase relative to the absence of the therapy with the modified polypeptide containing at least one ornithine residue).

A problem with forced vital capacity determination is that the forced vital capacity maneuver (forced exhalation from maximum inspiration to maximum expiration) is largely technique dependent. In other words, a given subject may produce different FVC values during a sequence of consecutive FVC maneuvers. The forced expiratory lung flow (FEF) 25-75 or FEF determined over the midportion of a forced exhalation maneuver tends to be less technique dependent than the FVC. Similarly, the FEV1 tends to be less technique-dependent than FVC. Thus, an increase (such as a statistically significant increase), as determined by mathematical formulas well known to those skilled in the art, in the FEF 25-75 or FEV1 reflects a decrease in bronchoconstriction, and indicates that the polypeptide and NAD therapy (administered with or without an ART), or therapy with modified polypeptide containing at least one ornithine residue is effective (for example an increase relative to the absence of the therapy with the modified polypeptide containing at least one ornithine residue).

In addition to measuring volumes of exhaled air as indices of pulmonary function, the flow in liters per minute measured over differing portions of the expiratory cycle can be useful in determining the status of a subject's pulmonary function. In particular, the peak expiratory flow, taken as the highest airflow rate in liters per minute during a forced maximal exhalation, is well correlated with overall pulmonary function in a patient with asthma and other respiratory diseases. Thus, an increase (such as a statistically significant increase), as determined by mathematical formulas well known to those skilled in the art, in the peak expiratory flow following administration of the polypeptide and NAD (administered with or without an ART), or administration of the modified polypeptide containing at least one ornithine residue, indicates that the therapy is effective (for example an increase relative to the absence of the therapy with the polypeptide and NAD (administered with or without an ART) or the modified polypeptide containing at least one ornithine residue).

IV. In Vitro Method of Producing Ornithine-Containing Polypeptide

Disclosed herein is an in vitro method of producing a polypeptide with altered activity that includes at least one ornithine residue in place of an arginine residue. Polypeptides produced by such methods can be used in the therapeutic methods provided herein to treat pulmonary disease. The method includes contacting a polypeptide of interest including at least one arginine residue susceptible to ADP-ribosylation with NAD and an arginine-specific mono-ADP-ribosyltransferase (for example, ART1) to produce a polypeptide including at least one ADP-ribosylated arginine. The ADP-ribosylated polypeptide is incubated under conditions sufficient for conversion of the at least one ADP-ribosylated arginine to ornithine, and the ornithine-containing polypeptide is isolated. In some examples, the polypeptide includes an enzyme, a cytokine, a chemokine, an anti-inflammatory peptide, a receptor ligand, a hormone, an antigen, or an antibody. In particular examples, the polypeptide includes a defensin.

An ADP-ribose is covalently attached to another compound by ADP-ribosylation. In one embodiment, the ART substrate (the source of the ADP-ribose) is NAD. ADP-ribose acceptors of known mammalian ARTs include basic and arginine-rich proteins that are involved in host defense (e.g., lymphocyte activation, neutrophil chemotaxis). ADP-ribose acceptors that contain an arginine can also be modified by an ART, but need not be arginine rich or basic. ADP-ribose acceptors include proteins with arginine residues, and thus include, but are not limited to, alpha defensins (for example, HNP-1, HNP-2, HNP-3, HNP-4, HD-5, HD-6, Def-X), beta defensins (for example, hBD1, hBD-2, hBD-3, hBD-4), major basic protein, eosinophil cationic protein, cathelicidin antimicrobial peptide (e.g., hCAP18), and lysozyme. Thus, an ADP-ribosyltransferase (such as ART1) can be used to produce ADP-ribosylated polypeptides, such as defensin polypeptides.

In one example, the polypeptide, such as a defensin, which includes at least one arginine residue (such as one, two, three, or four arginine residues) that are susceptible to ADP-ribosylation is contacted with NAD and an ART. In a particular example, the polypeptide is a defensin such as HNP-1 (for example, SEQ ID NO: 2). ART (such as ART1) catalyzes transfer of an ADP-ribose from NAD to an arginine residue in the polypeptide, such as HNP-1.

In some examples, the polypeptide, such as a defensin, is ADP-ribosylated on at least one, at least two, at least three, or at least four arginine residues. In a particular example, HNP-1 is ADP-ribosylated on an arginine at position 14 of SEQ ID NO: 2. In further examples, HNP-1 is ADP-ribosylated on an arginine at position 24 of SEQ ID NO: 2. In additional examples, HNP-1 is ADP-ribosylated at an arginine at position 14 and an arginine at position 24 of SEQ ID NO: 2.

The disclosed methods include contacting a polypeptide such as a defensin with at least one arginine residue susceptible to ADP-ribosylation (for example, HNP-1) with NAD and an arginine-specific mono-ADP-ribosyltransferase (for example, ART1) to produce a polypeptide including at least one ADP-ribosylated arginine. In some examples, purified polypeptide, such as a defensin (such as recombinantly produced defensin polypeptide or synthetic defensin polypeptide) is utilized. In one example, synthetic HNP-1 is utilized (see e.g., Raj et al., Biochem. J. 347:633-641, 2000). Synthetic defensins are commercially available (for example, Bachem, Torrance, Calif.; Catalog Nos. H-9855 (hHNP-1); H-9005 (hHNP-2); and H-9860 (hHNP-3)). In some examples, about 1 nmol to 1 μmol (for example, about 3 nmol, 5 nmol, 10 nmol, 50 nmol, 100 nmol, 250 nmol, 500 nmol, or 1 μmol) of polypeptide, such as a defensin polypeptide, is contacted with NAD and ART to produce ADP-ribosylated polypeptide. In particular examples, about 1 nmol to 25 nmol HNP-1 polypeptide (for example, about 3 nmol, 5 nmol, 10 nmol, 15 nmol, or 20 nmol) is ADP-ribosylated.

NAD is the source of ADP-ribose for ADP-ribosylation of a polypeptide, such as a defensin polypeptide by ARTs. NAD is commercially available (for example, Sigma-Aldrich, St. Louis, Mo.; JT Baker, Phillipsburg, N.J.; Amresco, Solon, Ohio). In some examples, about 1 mM to about 25 mM NAD (for example, about 2 mM, about 5 mM, about 10 mM, about 15 mM, or about 20 mM) is incubated with the polypeptide and ART for ADP-ribosylation of the polypeptide.

ART catalyzes the transfer of ADP-ribose from NAD to a polypeptide, such as a defensin polypeptide. Mammalian ART (for example, ART1, ART2, ART3, ART4, or ART5) may be recombinantly expressed in bacteria or mammalian cells and purified for use in the in vitro methods described herein. In some examples, mammalian ART1, such as human ART1 (for example, GenBank Accession No. NP_004305, incorporated herein by reference as present in GenBank on Sep. 10, 2009) or mouse ART1 (for example, GenBank Accession No. NP_033840, incorporated herein by reference as present in GenBank on Sep. 10, 2009) is used.

In some examples, mammalian ART1 can be introduced into a bacterial expression vector and produced in E. coli. See, e.g., Paone et al., Proc. Natl. Acad. Sci. USA 99:8231-8235, 2002. In other examples, mammalian ART1 may be introduced into a mammalian expression vector and produced in a mammalian cell line. See, e.g., Paone et al., J. Biol. Chem. 281:17051-17060, 2006. In a particular, non-limiting example, rat mammary adenocarcinoma (NMU) cells are transfected with a plasmid containing mouse ART1. ART1 is collected following treatment of intact cells with phosphatidylinositol-specific phospholipase C (PI-PLC; for example, 0.05 U PI-PLC for 1 hour). Cells are sedimented, and the supernatant containing released ART1 is collected.

ART activity can be assessed by monitoring transfer of ADP-ribose to agmatine or by measuring the formation of nicotinamide from NAD (see, e.g., Weng et al., J. Biol. Chem. 274:31797-31803, 1999; Okazaki et al., Blood. 88:915-21, 1996). In some examples, about 1 nmol/h to about 20 nmol/h ART (for example, about 1.5 nmol/h, about 2 nmol/h, about 5 nmol/h, about 10 nmol/h, about 12 nmol/h or about 15 nmol/h) is incubated with a polypeptide (such as a defensin polypeptide) and NAD for ADP-ribosylation of the polypeptide.

Although exemplary amounts of polypeptide (such as HNP-1), NAD, and ART are provided that can be used for in vitro ADP-ribosylation of a polypeptide, one of skill in the art may modify the amounts in the ADP-ribosylation reaction. For example, the reaction may be scaled up using conventional techniques known to one of skill in the art in order to increase the amount of ADP-ribosylated defensin that is produced.

In the disclosed methods, the polypeptide, such as the defensin, is contacted in vitro with NAD and ART to produce ADP-ribosylated polypeptide. Conditions for ADP-ribosylation of a polypeptide in vitro are known to one of skill in the art. In particular examples, the reaction is carried out at a pH and temperature suitable for ART activity. In some examples, the reaction is carried out at approximately physiological pH, such as about pH 7 to 8 (for example, about pH 7.0, 7.1, 7.2, 7.3, 7.4, 7.5, 7.6, 7.7., 7.8, 7.9, or 8.0) and at about 30° C. to about 37° C. (for example, about 30° C., 31° C., 32° C., 33° C., 34° C., 35° C., 36° C., or 37° C.). The polypeptide, NAD, and ART are incubated for a sufficient period of time for ADP-ribose to be transferred to the polypeptide. In some examples, the incubation is for about 2 hours to 24 hours (for example, about 4 hours, 8 hours, 12 hours, 16 hours, 18 hours, or 24 hours), such as overnight.

In a specific, non-limiting example, about 10 nmol HNP-1 polypeptide is mixed with about 5 mM NAD and about 12 nmol/h ART1 in potassium phosphate buffer of about pH 7.5, and the mixture is incubated overnight at about 30° C.

The ADP-ribosylated polypeptide (such as ADP-ribosylated defensin, for example HNP-1) is incubated under conditions sufficient for conversion of at least one ADP-ribosylated arginine residue to an ornithine residue. As disclosed herein, the conversion of ADP-ribosylated arginine HNP-1 to ornithine HNP-1 may be a non-enzymatic process. The conditions sufficient for conversion of ADP-ribosylated arginine to ornithine in vitro include appropriate pH, time, and temperature, as described herein.

In a particular example, an ADP-ribosylated arginine at position 14 of HNP-1 (for example, position 14 of SEQ ID NO: 2) is converted to an ornithine residue. In further examples, an ADP-ribosylated arginine at position 24 of HNP-1 (for example, position 24 of SEQ ID NO: 2) is converted to an ornithine residue. In additional examples, ADP-ribosylated arginine residues at position 14 and position 24 of HNP-1 (for example, positions 14 and 24 of SEQ ID NO: 2) are both converted to an ornithine residue. However, any ADP-ribosylated arginine residue in a polypeptide (such as an alpha defensin polypeptide) can be converted to an ornithine residue by the methods described herein.

In some examples, the conditions sufficient for conversion of at least one ADP-ribosylated arginine residue to an ornithine residue include incubating the ADP-ribosylated protein (such as ADP-ribosylated HNP-1) in a solution having a pH of about 7 to 9 (such as about pH 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). In particular examples, the ADP-ribosylated protein is incubated in a solution having a pH of about 7.5, about 8.0, or about 9.0. One of skill in the art can select an appropriate solution for conversion of ADP-ribosylated arginine to ornithine (for example, phosphate, tris, acetate, citrate, or other buffers). In a particular example, the solution includes potassium phosphate, such as about 1 mM to about 500 mM (for example, about 10 mM to 100 mM) potassium phosphate, for example about 50 mM potassium phosphate.

In some examples, the conditions for conversion of ADP-ribosylated arginine to ornithine include incubating the ADP-ribosylated protein (such as a defensin, for example HNP-1) for a sufficient period of time for at least one ADP-ribosylated arginine to be converted to an ornithine. In particular examples, the incubation time is about 2 hours to about 168 hours (for example, about 4 hours, about 8 hours, about 12 hours, about 16 hours, about 18 hours, about 24 hours, about 36 hours, about 48 hours, about 72 hours, about 96 hours, about 120 hours, about 144 hours, or about 168 hours). In one example, ADP-ribosylated protein, such as HNP-1 (for example mono-ADP-ribosylated HNP-1 or di-ADP-ribosylated HNP-1) is incubated overnight, for example, about 16 to 18 hours, such that at least one ADP-ribosylated arginine is converted to an ornithine. In another example, ADP-ribosylated HNP-1 (such as mono-ADP-ribosylated-HNP-1 or di-ADP-ribosylated-HNP-1) is incubated for about 24 hours, such that at least one ADP-ribosylated arginine is converted to an ornithine.

In some examples, the conditions for conversion of ADP-ribosylated arginine to ornithine include incubating the ADP-ribosylated protein (such as ADP-ribosylated HNP-1) at a temperature sufficient for at least one ADP-ribosylated arginine to be converted to an ornithine. In some examples, the incubation temperature is about 30° C. to about 37° C. (for example, about 30° C., 31° C., 32° C., 33° C., 34° C., 35° C., 36° C., or 37° C.).

In one particular, non-limiting example, ADP-ribosylated defensin (such as mono-ADP-ribosylated HNP-1 or di-ADP-ribosylated HNP-1) is incubated in 50 mM potassium phosphate, pH 9 at 30° C. overnight. In another example, ADP-ribosylated defensin (such as mono-ADP-ribosylated HNP-1 or di-ADP-ribosylated HNP-1) is incubated in 50 mM potassium phosphate, pH 7.5 at 30° C. overnight.

In some examples, ADP-ribosylated polypeptide, such as a defensin (for example mono-ADP-ribosylated HNP-1 or di-ADP-ribosylated HNP-1) is purified prior to incubation under conditions sufficient for conversion of at least one ADP-ribosylated arginine residue to an ornithine residue. Methods of purifying ADP-ribosylated proteins (such as defensins) are well known to one of skill in the art. In some examples, ADP-ribosylated protein (for example, mono-ADP-ribosylated HNP-1 and/or di-ADP-ribosylated HNP-1) can be purified using chromatographic methods (for example, HPLC or affinity chromatography). In other examples, the polypeptide such as the defensin can be a recombinant protein that includes a component that facilitates protein purification, such as glutathione S-transferase, a polyhistidine tag, or a FLAG or Myc tag. In a particular example, the ADP-ribosylated protein is purified by HPLC.

In other examples, the conditions for ADP-ribosylation of at least one arginine residue of a polypeptide by an ART in the presence of NAD are the same as those sufficient for conversion of at least one ADP-ribosylated arginine residue in the polypeptide to an ornithine residue. In this case, ADP-ribosylated polypeptide, such as the defensin is not purified prior to conversion of ADP-ribosylated arginine to ornithine, rather, both reactions occur in a single incubation. In a particular, non-limiting example, 10 nmol HNP-1 is incubated with 5 mM NAD and 12 nmol/h ART1 in 50 mM potassium phosphate, pH 7.5 overnight at 30° C.

The ornithine-containing polypeptide, such as the defensin (such as ornithine-containing HNP-1) produced as described herein may be isolated or purified. Methods of purifying polypeptides, such as a polypeptide including at least one ornithine residue, are well known to one of skill in the art. In particular examples, the ornithine-containing protein (such as HNP-1 with at least one arginine residue replaced with an ornithine residue) is purified using chromatographic methods, (for example, HPLC or affinity chromatography). In other examples, the ornithine-containing defensin polypeptide may be a recombinant protein that includes a component that facilitates protein purification, such as glutathione S-transferase, a polyhistidine tag, or a FLAG or Myc tag. In a particular example, the ornithine-containing protein is purified by HPLC.

In some examples, the method further includes measuring or assessing an activity of the modified polypeptide. The modification of an arginine residue (for example, ADP-ribosylation) in a polypeptide (such as a defensin) can alter its activity (such as antimicrobial activity) and/or modify an immune response (see, e.g., Paone et al., *Proc. Natl. Acad. Sci. USA* 99:8231-8235, 2002; U.S. Pat. No. 7,511,015). In some examples, the ornithine-containing polypeptide (such as ornithine-containing HNP-1, for example, HNP-1 including at least one ornithine at amino acid position 14 and/or 24 of SEQ ID NO: 2) has reduced antimicrobial activity. In several non-limiting examples, the decrease in antimicrobial activity is at least about a 20% decrease, at least about a 50% decrease, at least about a 75% decrease, at least about an 80% decrease, at least about a 90% decrease, at least about a 95% decrease, at least about a 98% decrease, or at least about a 100% decrease, for example relative to a non-ornithine containing HNP-1. The antimicrobial activity can be antibacterial, antifungal, or antiviral activity. Antimicrobial activity can be determined by any method known to one of skill in the art. In one example, the antimicrobial activity is lysis of bacteria, fungi, or viruses.

In another example, the altered antimicrobial activity is an increase in cytokine production. The increase in cytokine production can be an increase in cytokine secretion, expression, and/or release. In several non-limiting examples, the increase in cytokine production is at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase, for example relative to a non-ornithine containing HNP-1. Cytokine production can be measured by any method known to one of skill in the art. In one specific, non-limiting example, cytokine release is measured by enzyme-linked immunosorbent assay (ELISA). In a particular example, the cytokine is interleukin-8 (IL-8).

In a further example, the altered antimicrobial activity is an increase in the recruitment of inflammatory cells. Recruitment of inflammatory cells can be determined by any method known to one of skill in the art. In one specific, non-limiting example, the inflammatory cells are neutrophils. In a further embodiment, the altered antimicrobial activity is an increase in inflammatory cell chemotaxis. In several non-limiting examples, the increase in inflammatory cell chemotaxis is at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase, for example relative to a non-ornithine containing HNP-1. In one specific, non-limiting example the inflammatory cells are T cells. T cell chemotaxis can be measured by any means known to one of skill in the art, for example, measuring the length of migration of T cells, the number of migrating T cells, or both. In a specific example, T cell migration is measured in vitro, such as by measuring T cell migration from one cell culture chamber to another cell culture chamber through a porous membrane.

In some examples, the antimicrobial activity of a modified alpha defensin is altered as compared to an unmodified (native) alpha defensin polypeptide or an ADP-ribosylated alpha defensin polypeptide. In one specific, non-limiting example, the modified alpha defensin is an ornithine-containing HNP-1 polypeptide and the unmodified alpha defensin is unmodified HNP-1 polypeptide. In another specific, non-limiting example, the modified alpha defensin is an ornithine-containing HNP-1 polypeptide and the ADP-ribosylated alpha defensin is ADP-ribosylated HNP-1 polypeptide.

V. Pharmaceutical Compositions and Administration

Pharmaceutical compositions that include a polypeptide with at least one arginine residue susceptible to ADP-ribosylation, or a modified polypeptide with at least one ornithine residue in place of an arginine residue, and/or pharmaceutical compositions that include NAD can be formulated with an appropriate solid or liquid carrier, depending upon the particular mode of administration chosen. A specific, non-limiting example of a polypeptide including at least one arginine residue susceptible to ADP-ribosylation includes HNP-1 polypeptide (for example, SEQ ID NO: 2). A specific, non-limiting example of a modified polypeptide including at least one ornithine residue in place of an arginine residue includes an HNP-1 polypeptide including an ornithine residue at amino acid position 14 and/or 24 of SEQ ID NO: 2. In one example, the pharmaceutical composition includes at least one polypeptide (such as a defensin, for example, HNP-1) and NAD. In additional examples, the pharmaceutical composition further includes an ART (such as ART1, ART2, or ART5).

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{St}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

Medicinal and pharmaceutical agents, for instance immunostimulants, also can be included Immunostimulants include, but are not limited to, cytokines, such as Macrophage Inflammatory Protein (MIP)—, IL-1, IL-8, IL-10, granulocyte-macrophage colony stimulating factor (GM-CSF), granulocyte colony stimulating factor (G-CSF), neurokinin, and tumor necrosis factor-alpha (TNFα), for example.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include a polypeptide (such as a defensin, for example, HNP-1) including at least one arginine residue susceptible to ADP-ribosylation or a modified polypeptide including at least one ornithine residue in place of an arginine residue (such as a modified defensin) can be formulated in unit dosage form, suitable for individual administration of precise dosages. In one specific, non-limiting example, a unit dosage can contain from about 1 ng to about 1 mg of HNP-1 polypeptide. In another non-limiting example, a unit dosage can contain from about 0.5 μM to about 200 mM NAD. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans or other animals on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years.

Site-specific administration of the disclosed compounds can be used, for instance by administering a NAD and/or a polypeptide to the lungs or respiratory tract to treat a subject with pulmonary disease. By way of example, one method of administration to the lungs of an individual is by inhalation through the use of a nebulizer or inhaler. For example, the NAD and/or polypeptide is formulated in an aerosol or particulate and drawn into the lungs using a standard nebulizer well known to those skilled in the art. Other routes of administration to the lungs or respiratory tract include bronchial, intranasal, or other inhalatory routes. In some examples the NAD and/or polypeptide is administered by inhalation (for example, by inhaling an aerosol); direct installation in the lung via a bronchoscope, endotracheal tube, or an artificial ventilation device; nasal administration (intranasal or transnasal); bronchial, or intratracheally (for example, by injection directly into the trachea or tracheostomy).

A therapeutically effective amount of NAD administered by inhalation in conjunction with administration of a polypeptide (such as a defensin, for example HNP-1) having at least one arginine residue susceptible to ADP-ribosylation can be the amount of NAD necessary to treat a pulmonary disease of a subject, for example, an amount necessary to increase ADP-ribosylation of a polypeptide and its subsequent conversion to a polypeptide containing at least one ornithine residue in place of an arginine residue.

A therapeutically effective amount of a polypeptide including at least one arginine residue susceptible to ADP-ribosylation and NAD (administered with or without an ART polypeptide) or a modified polypeptide including at least one ornithine residue in place of an arginine residue, can be the amount of a polypeptide (such as a defensin, for example, HNP-1) including at least one arginine residue susceptible to ADP-ribosylation and NAD or a modified polypeptide (such as a defensin, for example, HNP-1) including at least one ornithine residue in place of an arginine residue necessary to treat a pulmonary disease of a subject.

A therapeutically effective amount of a polypeptide including at least one arginine residue susceptible to ADP-ribosylation and NAD (administered with or without an ART polypeptide) or a modified polypeptide including at least one ornithine residue in place of an arginine residue, can be administered in a single dose, or in several doses, for example daily, during a course of treatment. However, the therapeutically effective amount will be dependent on the subject being treated, the severity and type of the affliction, and the manner of administration of the therapeutic(s).

The present disclosure also includes combinations of a polypeptide including at least one arginine residue susceptible to ADP-ribosylation and NAD (administered with or without ART) or a modified polypeptide including at least one ornithine residue in place of an arginine residue, with one or more other agents useful in the treatment of pulmonary disease. For example, the compounds of this disclosure can be administered in combination with effective doses of modified antimicrobial agents other than defensins, immunostimulants, anti-tumor agents, anti-inflammatory agents, anti-infectives, and/or vaccines. The term "administration in combination" or "co-administration" refers to both concurrent and sequential administration of the active agents.

In one example, a polypeptide including at least one arginine residue susceptible to ADP-ribosylation and NAD (administered with or without ART) or a modified polypeptide including at least one ornithine residue in place of an arginine residue may be co-administered with therapeutic that is effective to decrease the viscosity of pulmonary secretions, such as a DNase (for example, DNase I or DNase II). See, e.g., U.S. Pat. No. 7,297,526. The DNase may be administered by any suitable route, for example, by inhalation or direct instillation in the nasotracheal or endotracheal tubes in an intubated patient. In a particular example, a patient having a pulmonary disease with abnormal or viscous secretions (including, but not limited to pneumonia, chronic bronchitis, cystic fibrosis, or asthma) is treated with a polypeptide (such as a defensin) including at least one residue susceptible to ADP-ribosylation, NAD and DNase. In another example, a patient having a pulmonary disease with abnormal or viscous secretions (including, but not limited to pneumonia, chronic bronchitis, cystic fibrosis, or asthma) is treated with a polypeptide (such as a defensin) including at least one residue susceptible to ADP-ribosylation, NAD, ART, and DNase. In a further example, a patient having a pulmonary disease with abnormal or viscous secretions (including, but not limited to pneumonia, chronic bronchitis, cystic fibrosis, or asthma) is treated with a polypeptide (such as a defensin) including at least one ornithine residue in place of an arginine residue and DNase.

A subject that has a pulmonary disease (such as cystic fibrosis, emphysema, asthma, sarcoidosis, chronic bronchitis, bronchopulmonary dysplasia, pulmonary fibrosis, pneumonia, or adult respiratory distress syndrome), will be a candidate for treatment using the therapeutic methods disclosed herein.

The disclosure is illustrated by the following non-limiting Examples.

EXAMPLES

Example 1

Conversion of ADP-Ribosylated Arginine to Ornithine in HNP-1

This example describes the non-enzymatic conversion of ADP-ribosylated arginine in HNP-1 to ornithine.

Methods

ADP-Ribosylation of HNP-1:

Rat mammary adenocarcinoma (NMU) cells transfected with plasmids containing mART1 were grown in Eagle's minimal essential medium with 10% fetal bovine serum (Invitrogen) and 0.5 mg/ml Geneticin (G-418). Cells were purchased from American Type Culture Collection (Manassas, Va.). Protein released from the cells by phosphatidyl inositol-specific phospholipase C, collected in the medium for ADP-ribosyltransferase activity was assayed by quantifying the transfer of ADP-ribose to agmatine in standard assays as described (Paone et al., *J. Biol. Chem.*, 281:17054-17060, 2006).

HNP-1 was incubated overnight at 30° C. with 5 mM NAD in 150 µl of 50 mM potassium phosphate, pH 7.5 and ART1. Reactions were terminated by addition of guanidine HCl to a final concentration of 6 M. Products were separated by HPLC and analyzed by mass spectrometry (MS).

Preparation of ADP-Ribosyl-[$^{14}$C]Arginine:

Cholera toxin A subunit (60 µg), 30 mM dithiothreitol (DTT), 10 mM NAD, and 10 mM arginine (0.5 µCi $^{14}$C/assay) were incubated overnight at 30° C. with 30 µg ovalbumin in 20 mM potassium phosphate, pH 7.5, (volume 300 µl). Reaction products were separated on a strong anion exchange (SAX) column (DuPont, Wilmington, Del.) by gradient elution (Paone et al., *J. Biol. Chem.*, 281:17054-17060, 2006). Radioactive peaks were collected, vacuum-concentrated, and applied to a Discovery BioWide Pore C18 RP-HPLC column (Supelco, Bellefonte, Pa.) equilibrated for 15 min with HPLC water, 0.05% TFA, (flow=0.8 ml/min), followed by a 5 min linear gradient of 0 to 100% acetonitrile. Peaks, monitored by absorbance at 254 nm and radioactivity identified as ADP-ribosyl-[$^{14}$C]arginine were confirmed by MS analysis. Samples (25 µl) of ADP-ribosyl-[$^{14}$C]arginine were vacuum-dried, dissolved in 200 µl 6 N HCl (Fluka), and hydrolyzed under nitrogen (155° C., 45 min) to release arginine. The hydrolysate was vacuum-dried, dissolved in 25 μl 0.05% TFA and subjected to o-phthalaldehyde (OPA) derivatization (Agilent Technologies, Santa Clara, Calif.) before HPLC separation. The arginine peak was quantified by absorbance at 338 nm and fluorescence (340 nm excitation/450 nm emission) then compared to a standard curve. Similarly, the amount of ornithine following incubation of ADP-ribosyl-larginine samples was determined by OPA derivatization and compared to a standard curve.

Amino Acid Analysis:

HNP-1 (Bachem, Torrance, Calif.) was vacuum-dried, dissolved in 200 μl of 6N HCl plus 5 μl of 40 mM DTT before hydrolysis under nitrogen at 155° C. for 45 mM The hydrolysate was vacuum-dried and solubilized in 25 μl water, 0.05% TFA before OPA pre-column automated derivatization. The conditions for the derivatization reaction and the HPLC separation (with the modification below) are described in Agilent Technologies Technical Note (Publication number 5980-1193EN). The HPLC column, Eclipse-AAA (4.6×150 mm, 5 μm particle size) was equilibrated with mobile phase A, 40 mM sodium dibasic phosphate buffer pH 7.8 using a linear gradient of 0 to 40% of phase B, acetonitrile:MeOH:water (45:45:10) for 1.9-15 mM; 15-18.1 mM gradient to 57% B, 18.1-18.6 mM gradient to 100% B.

MS and Sequence Analysis:

HNP-1 was reduced, cleaved by trypsin, and analyzed by reverse phase chromatography-mass spectrometry as described (Paone et al., Proc. Natl. Acad. Sci. USA 99:8231-8235, 2002), except that the reverse phase column was a Zorbax 300SB-C18, 2.1×50 mm, 3.5 micron, and the mass spectrometer was an Agilent model G1969 with a time of flight detector. Mass spectra were deconvoluted with Agilent software MassHunter version 2, and the fraction of each species was calculated from the areas of the deconvoluted peaks.

Results

Figure 1:
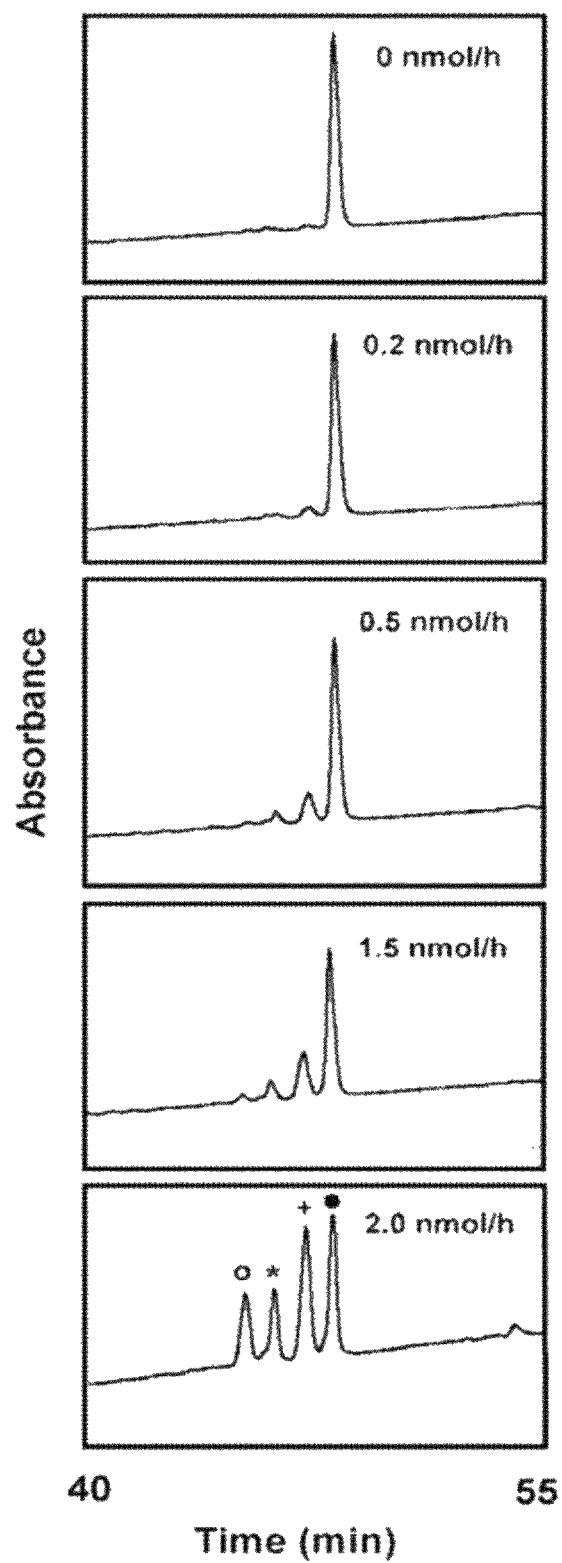
FIG. 1 is a series of chromatograms showing reverse phase-high performance liquid chromatography (RP-HPLC) separation of reaction products from incubation of 3 nmol HNP-1 and 5 mM NAD with the indicated amounts of ART1 at 30° C. overnight. Peaks were identified by mass spectrometry (MS)
Figure 2:
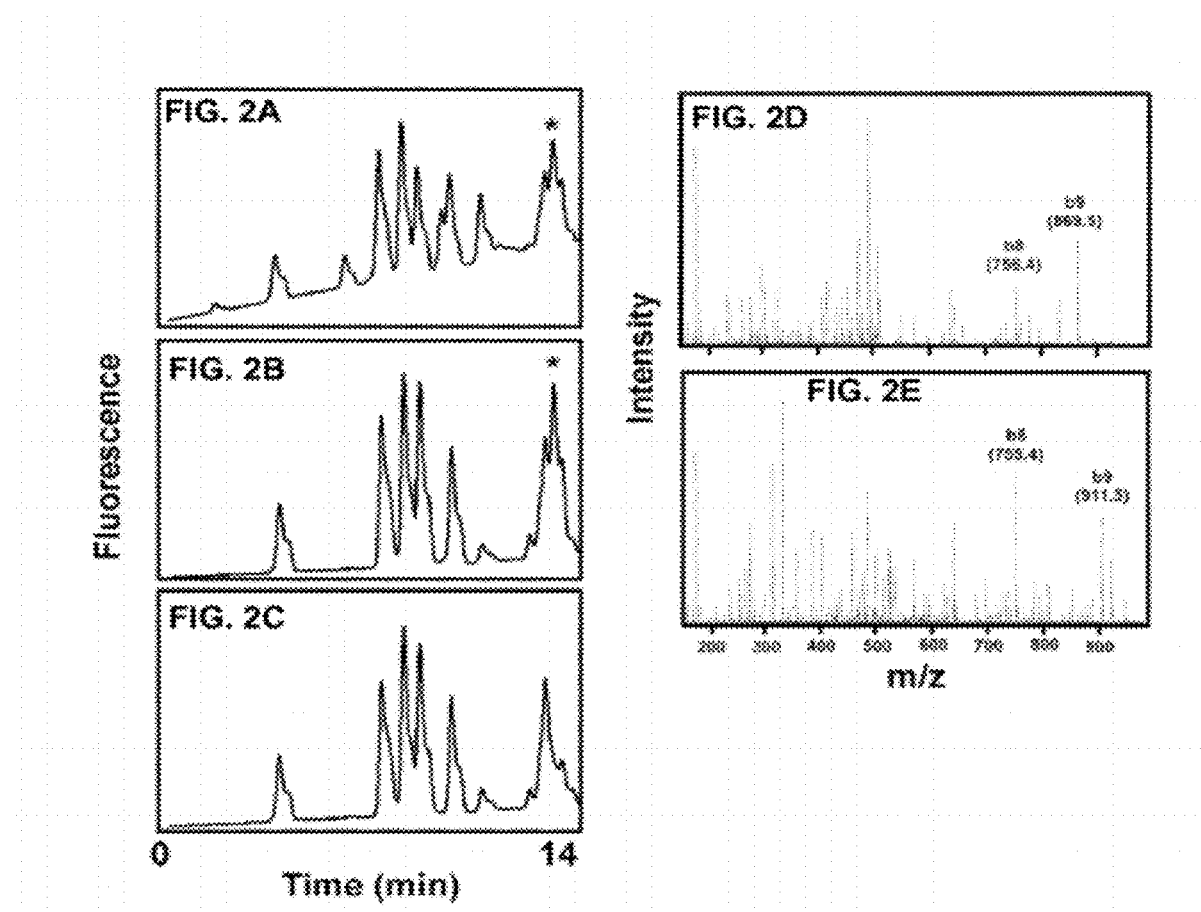

HNP-1 was ADP-ribosylated in vitro using purified ART1. HPLC analysis of the reaction products identified HNP-1, mono-ADP-ribosylated HNP-1, and di-ADP-ribosylated HNP-1 (FIG. 1). Incubation of ART1 (2 nmol/h activity) and HNP-1 for 24 hours at 30° C. decreased the amount of di-ADP-ribosylated HNP-1 and increased the amount of a fourth HPLC peak (FIG. 1). MS analysis identified HNP-1, mono-ADP-HNP-1 ribosylated on arginine 14, and di-ribosylated HNP-1 with a second modification of arginine 24. The purified 3940 Da product, identified as ADP-ribosylated-HNP-1-ornithine, mapped to position 14 was subjected to acid hydrolysis Amino acid analysis confirmed the presence of ornithine in the modified, but not in the substrate HNP-1 (FIG. 2). Since arginine 14 was the site of the initial ADP-ribosylation, it appeared that ADP-ribosyl-arginine was the precursor of ornithine in HNP-1. Amounts of modified HNP-1-ornithine recovered in the reaction mix increased with incubation time, reaching about 26% after 168 hours, consistent with non-enzymatic conversion of arginine to ornithine (FIG. 3).

To verify that ART1 (or an enzymatic contaminant) was not required for ornithine formation, HPLC-purified mono- and di-modified HNP-1 were incubated for 24 hours at 37° C. at pH 7 or 9 and the reaction products were analyzed by HPLC (FIG. 4, Table 1). Di-ADP-ribosylated-HNP-1 degraded to mono-ADP-ribosylated-HNP-1-ornithine of 3940 molecular mass at pH 7 and the amount was greater at pH 9 (FIG. 4A-D). About 50% of di-ADP-ribosylated-HNP-1 degraded to mono-ADP-ribosylated-HNP-1-ornithine at pH 9, with ADP-ribosylated arginine 14 and ornithine at position 24 or ADP-ribosylated arginine 24 and ornithine at position 14. Purified mono-ADP-ribosylated-HNP-1 was converted to HNP-1-ornithine (3399.5 Da) under the same conditions at pH 7 and the amount was greater at pH 9 (FIG. 4E-G).

TABLE 1

MS analysis of mono- and di-ADP-ribosyl-HNP-1 incubated at pH 7 or 9

| | pH | Time (h) | HNP | ADPR-HNP | HNP-Orn | Di-Orn-HNP | ADPR-HNP-Orn | Di-ADPR-HNP |
|---|---|---|---|---|---|---|---|---|
| ADPR-HNP | 7 | 0 | 0 | 100 | 0 | 0 | 0 | 0 |
| ADPR-HNP | 7 | 24 | 0 | 82 ± 13 | 18 ± 13 | 0 | 0 | 0 |
| ADPR-HNP | 9 | 0 | 0 | 100 | 0 | 0 | 0 | 0 |
| ADPR-HNP | 9 | 24 | 0 | 61 ± 9 | 39 ± 9 | 0 | 0 | 0 |
| Di-ADPR-HNP | 7 | 0 | 0 | 0 | 0 | 0 | 0 | 100 |
| Di-ADPR-HNP | 7 | 24 | 0 | 0 | 0 | 1 ± 1 | 32 ± 17 | 67 ± 18 |
| Di-ADPR-HNP | 9 | 0 | 0 | 0 | 0 | 0 | 13 | 87 |
| Di-ADPR-HNP | 9 | 24 | 0 | 0 | 0 | 9 ± 3 | 55 ± 3 | 36 ± 0 |

Values indicate the percent of each species at the end of the incubation

Arginase, found predominantly in liver, catalyzes the hydrolysis of arginine to ornithine in the urea cycle. The enzyme has been reported to require free arginine (Jenkinson et al., Comp. Biochem. Physiol. B Biochem. Mol. Biol. 114: 107-132, 1996). HNP-1 was tested as a potential substrate for arginase. HNP-1 (1.4 nmol), mono-ADP-ribosylated-HNP-1 (1 nmol), ADP-ribosylarginine (18 μM), and arginine (5 mM) were each incubated with manganese-activated arginase (0.7 U) at pH 9.5 in 200 μl for 10 minutes at 37° C. Identification of the products by amino acid analysis and MS identified ornithine only in the reaction that contained free arginine. This confirms that HNP-1 is not a substrate for arginase.

Ornithine has been found in acid hydrolysates of human skin collagen and lens crystalline in amounts that increase with the age of subjects from whom the proteins were isolated (Sell and Monnier, J. Biol. Chem. 279:54173-54184, 2004). The presence of ornithine in these proteins is believed to result from the reaction of reducing sugars with arginine residues to form advanced glycation end products (AGEs), followed by time-dependent breakdown of the AGEs to yield ornithine. Non-enzymatic modification of several proteins by sugars in vitro has been reported (Shapiro et al., J. Biol. Chem. 255:3120-3127, 1980; Sun et al., J. Agric. Food Chem. 52:1293-1299, 2004), but ornithine in a primary protein sequence has only been reported only in collagen as a result of age-related glycation. No ornithine was identified after incubation of arginine with free ADP-ribose (FIG. 5A); ornithine alone is shown in FIG. 5B. Arginine was cleaved from ADP-ribosylarginine incubated in 6N HCl at 37° C. for 24 hours (FIG. 5C). However, consistent with non-enzymatic conversion of modified arginine to ornithine, ADP-ribosylarginine generated ornithine when incubated at 37° C. at pH 9 for 24 hours (compare FIGS. 5D and 5E). These data demonstrated that the amino acid sequence of HNP-1 is not required for conversion of modified arginines to ornithine. In contrast to the enzymatic cleavage of ADP-ribosylarginine by ADP-ribosyl-arginine hydrolase-1 (ARH1) at carbon 1" of ADP-ribose, which releases ADP-ribose from arginine, the non-enzymatic hydrolysis of ADP-ribose-arginine at the guanidino carbon of arginine produced ornithine.

Amino acid analysis of ADP-ribosyl-[$^{14}$C]-arginine at time zero showed the presence of ADP-ribosyl-[$^{14}$C]-arginine and arginine (FIG. 5F) Amino acid analysis of ADP-ribosyl-[$^{14}$C]-arginine incubated for 24 hours at 37° C., pH 9 showed the accumulation of ornithine (FIGS. 5G and 5H). The maximal amount of ornithine quantified by amino acid analysis without prior acid hydrolysis was 21% of initial ADP-ribosylarginine after incubation at pH 9 for 24 hours. After incubation at pH 7 or pH 8, the amount of ornithine was less than at pH 9 and was generated at a slower rate.

Example 2

Isolation of Ornithine-Containing HNP-1 from Bronchoalveolar Lavage

This example describes the detection of ornithine containing HNP-1 in BALF from a patient with IPF.

Preparation of bronchoalveolar lavage fluid (BALF) was as previously described (Paone et al., *J. Biol. Chem.*, 281:17054-17060, 2006). The clinical protocol (protocol 99-H-0068) was approved by the National Institutes of Health Institutional Review Board. Written informed consent was obtained from all subjects. BALF samples were obtained from seven patients with IPF and four patients with asthma. Briefly, 8 ml of BALF was applied to LC-18 SUPELCLEAN™ SPE tubes (Sigma-Aldrich, St. Louis, Mo.) equilibrated in 10% isopropanol/0.1% TFA, washed, and eluted with 50% isopropanol/0.1% TFA. The eluted proteins were vacuum-concentrated before separation by RP-HPLC as described in Example 1.

Mono- and di-ADP-ribosylated-HNP-1 have previously been detected in BALF from patients with IPF and asthma (Paone et al., *J. Biol. Chem.* 281:17054-17060, 2006). In four of the seven IPF samples, a broad peak eluted at the retention time of HNP-1. MS analysis confirmed that one of the samples contained HNP-1 and consisted of 38.8% HNP-1, 32.1% di-ADP-ribosylated HNP-1, 20.8% ADP-ribosyl-HNP-1 and 8.3% ADP-ribosyl-HNP-1-ornithine. These data are consistent with the in vivo alteration of HNP-1 primary sequence. Of note, as with in vitro ADP-ribosyl-HNP-1, in the in vivo modified material, di-ADP-ribosylated HNP-1-ornithine was not detected, consistent with ornithine is not ADP-ribosylated by NAD: arginine ADP-ribosyltransferases. Experimentally arginine and agmatine served as substrates for ART1, but ornithine did not. HNP-1-ornithine was not detected in BALF from patients with asthma (n=4); of the four patients, one had both di- and mono-ADP-ribosylated HNP-1.

Example 3

Treatment of Pulmonary Disease with Defensin and NAD

This example describes exemplary methods for treating a subject with pulmonary disease with a defensin polypeptide and NAD. However, one skilled in the art will appreciate that methods that deviate from these specific methods can also be used to successfully treat pulmonary disease.

Based upon the teaching disclosed herein, pulmonary disease (for example, cystic fibrosis, emphysema, asthma, sarcoidosis, chronic bronchitis, bronchopulmonary dysplasia, pulmonary fibrosis, pneumonia, or adult respiratory distress syndrome), can be treated by administering a therapeutically effective amount of a defensin polypeptide including at least one arginine residue susceptible to ADP-ribosylation and NAD, wherein the NAD is administered by inhalation.

In one example, a clinical trial includes half of the subjects following an established protocol for treatment of pulmonary disease or alternatively, a placebo control. The other half is treated by administering a defensin polypeptide including at least one arginine residue susceptible to ADP-ribosylation and NAD, wherein the NAD is administered by inhalation.

A therapeutically effective dose of the defensin polypeptide including at least one arginine residue susceptible to ADP-ribosylation and a therapeutically effective dose of NAD is administered to the subject (such as a subject either at risk for developing a pulmonary disease or known to have a pulmonary disease). Additional agents, such as immune stimulatory agents, can also be administered to the subject simultaneously, prior to, or following administration of the disclosed agents. The NAD is administered by inhalation. Administration of the defensin polypeptide can be achieved by any method known in the art, such as oral, inhalation, intravenous, intramuscular, intraperitoneal, or subcutaneous administration.

The amount of the defensin polypeptide and NAD administered to treat the pulmonary disease depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., the pulmonary disease) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly, or monthly repeated administration protocol). In one example, a therapeutic agent that includes a defensin polypeptide and NAD is administered via inhalation to a subject. As such, these compositions may be formulated with an inert diluent or with a pharmaceutically acceptable carrier. Administration of the therapeutic compositions can be taken long term (for example over a period of months or years).

Following the administration of one or more therapies, subjects having pulmonary disease can be monitored for reductions in one or more clinical symptoms associated with the pulmonary disease. In particular examples, subjects are analyzed one or more times, starting 7 days following treatment. Subjects can be monitored using any method known in the art. For example, lung function of the subject can be assessed by measuring forced vital capacity (FVC), forced expiratory volume (FEV), or forced expiratory flow (FEF). Other signs and symptoms of the particular pulmonary disease can also be assessed. A reduction in the clinical symptoms associated with the pulmonary disease, for example, improved lung function indicates the effectiveness of the treatment.

One of skill in the art will appreciate that the disclosed agents including defensin polypeptides (or modified defensin polypeptides including at least one ornithine) can be tested for safety in animals, and then used for clinical trials in animals or humans. In one example, animal models of pulmonary disease are employed to determine therapeutic value of the disclosed agents.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

The invention claimed is:

1. A method of treating a subject with a pulmonary disease, comprising administering to the subject a therapeutically effective amount of a modified human neutrophil peptide-1 (HNP-1) polypeptide, wherein the modified human HNP-1 polypeptide comprises the amino acid sequence consisting of SEQ ID NO: 2, wherein positions 14 and 24 are ornithine residues.

2. The method of claim 1, wherein the modified human HNP-1 polypeptide is administered by inhalation.

3. The method of claim 1, wherein the pulmonary disease comprises cystic fibrosis, emphysema, asthma, sarcoidosis, chronic bronchitis, bronchopulmonary dysplasia, pulmonary fibrosis, pneumonia, or adult respiratory distress syndrome.

4. The method of claim 3, wherein the pulmonary disease comprises pneumonia.

5. The method of claim 4, wherein the pneumonia is caused by a bacterial infection.

6. The method of claim 1, wherein the pulmonary disease is caused by an infection.

7. The method of claim 6, wherein the infection is a bacterial infection.

8. The method of claim 1, wherein the modified HNP-1 polypeptide exhibits antimicrobial activity and reduced cytotoxicity toward mammalian cells compared to an unmodified human HNP-1 of SEQ ID NO: 2.

9. The method of claim 1, wherein administration of the modified HNP-1 polypeptide increases cytokine production.

10. The method of claim 9, wherein the cytokine is interleukin (IL)-8.

* * * * *

```
                            SEQUENCE LISTING

<160> NUMBER OF SEQ ID NOS: 13

<210> SEQ ID NO 1
<211> LENGTH: 94
<212> TYPE: PRT
<213> ORGANISM: Homo sapiens

<400> SEQUENCE: 1

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Ala Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 2
<211> LENGTH: 30
<212> TYPE: PRT
<213> ORGANISM: Homo sapiens

<400> SEQUENCE: 2

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 3
<211> LENGTH: 29
<212> TYPE: PRT
<213> ORGANISM: Homo sapiens

<400> SEQUENCE: 3

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 4
<211> LENGTH: 94
<212> TYPE: PRT
<213> ORGANISM: Homo sapiens

<400> SEQUENCE: 4

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45
```

```
Trp Asp Glu Ser Leu Ala Pro Lys His Pro Gly Ser Arg Lys Asn Met
 50                  55                  60

Asp Cys Tyr Cys Arg Ile Pro Ala Cys Ile Ala Gly Glu Arg Arg Tyr
 65                  70                  75                  80

Gly Thr Cys Ile Tyr Gln Gly Arg Leu Trp Ala Phe Cys Cys
                 85                  90
```

```
<210> SEQ ID NO 5
<211> LENGTH: 30
<212> TYPE: PRT
<213> ORGANISM: Homo sapiens

<400> SEQUENCE: 5

Asp Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
                 20                  25                  30
```

```
<210> SEQ ID NO 6
<211> LENGTH: 97
<212> TYPE: PRT
<213> ORGANISM: Homo sapiens

<400> SEQUENCE: 6

Met Arg Ile Ile Ala Leu Leu Ala Ala Ile Leu Leu Val Ala Leu Gln
 1               5                  10                  15

Val Arg Ala Gly Pro Leu Gln Ala Arg Gly Asp Glu Ala Pro Gly Gln
                 20                  25                  30

Glu Gln Arg Gly Pro Glu Asp Gln Asp Ile Ser Ile Ser Phe Ala Trp
             35                  40                  45

Asp Lys Ser Ser Ala Leu Gln Val Ser Gly Ser Thr Arg Gly Met Val
 50                  55                  60

Cys Ser Cys Arg Leu Val Phe Cys Arg Arg Thr Glu Leu Arg Val Gly
 65                  70                  75                  80

Asn Cys Leu Ile Gly Gly Val Ser Phe Thr Tyr Cys Cys Thr Arg Val
                 85                  90                  95

Asp
```

```
<210> SEQ ID NO 7
<211> LENGTH: 34
<212> TYPE: PRT
<213> ORGANISM: Homo sapiens

<400> SEQUENCE: 7

Val Cys Ser Cys Arg Leu Val Phe Cys Arg Arg Thr Glu Leu Arg Val
 1               5                  10                  15

Gly Asn Cys Leu Ile Gly Gly Val Ser Phe Thr Tyr Cys Cys Thr Arg
                 20                  25                  30

Val Asp
```

```
<210> SEQ ID NO 8
<211> LENGTH: 94
<212> TYPE: PRT
<213> ORGANISM: Homo sapiens

<400> SEQUENCE: 8

Met Arg Thr Ile Ala Ile Leu Ala Ala Ile Leu Leu Val Ala Leu Gln
 1               5                  10                  15
```

-continued

Ala Gln Ala Glu Ser Leu Gln Glu Arg Ala Asp Glu Ala Thr Thr Gln
         20                  25                  30

Lys Gln Ser Gly Glu Asp Asn Gln Asp Leu Ala Ile Ser Phe Ala Gly
         35                  40                  45

Asn Gly Leu Ser Ala Leu Arg Thr Ser Gly Ser Gln Ala Arg Ala Thr
50                      55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
                85                  90

<210> SEQ ID NO 9
<211> LENGTH: 32
<212> TYPE: PRT
<213> ORGANISM: Homo sapiens

<400> SEQUENCE: 9

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30

<210> SEQ ID NO 10
<211> LENGTH: 100
<212> TYPE: PRT
<213> ORGANISM: Homo sapiens

<400> SEQUENCE: 10

Met Arg Thr Leu Thr Ile Leu Thr Ala Val Leu Leu Val Ala Leu Gln
1               5                   10                  15

Ala Lys Ala Glu Pro Leu Gln Ala Glu Asp Asp Pro Leu Gln Ala Lys
            20                  25                  30

Ala Tyr Glu Ala Asp Ala Gln Glu Gln Arg Gly Ala Asn Asp Gln Asp
         35                  40                  45

Phe Ala Val Ser Phe Ala Glu Asp Ala Ser Ser Ser Leu Arg Ala Leu
50                  55                  60

Gly Ser Thr Arg Ala Phe Thr Cys His Cys Arg Arg Ser Cys Tyr Ser
65                  70                  75                  80

Thr Glu Tyr Ser Tyr Gly Thr Cys Thr Val Met Gly Ile Asn His Arg
                85                  90                  95

Phe Cys Cys Leu
            100

<210> SEQ ID NO 11
<211> LENGTH: 30
<212> TYPE: PRT
<213> ORGANISM: Homo sapiens

<400> SEQUENCE: 11

Thr Cys His Cys Arg Arg Ser Cys Tyr Ser Thr Glu Tyr Ser Tyr Gly
1               5                   10                  15

Thr Cys Thr Val Met Gly Ile Asn His Arg Phe Cys Cys Leu
            20                  25                  30

<210> SEQ ID NO 12
<211> LENGTH: 94
<212> TYPE: PRT
<213> ORGANISM: Homo sapiens

<400> SEQUENCE: 12

```
Met Arg Thr Leu Thr Leu Leu Ser Ala Phe Leu Leu Val Ala Leu Gln
1               5                   10                  15

Ala Trp Ala Glu Pro Leu Gln Ala Arg Ala His Glu Met Pro Ala Gln
                20                  25                  30

Lys Gln Pro Pro Ala Asp Asp Gln Asp Val Val Ile Tyr Phe Ser Gly
            35                  40                  45

Asp Asp Ser Cys Ser Leu Gln Val Pro Gly Ser Thr Lys Gly Leu Ile
        50                  55                  60

Cys His Cys Arg Val Leu Tyr Cys Ile Phe Gly Glu His Leu Gly Gly
65                  70                  75                  80

Thr Cys Phe Ile Leu Gly Glu Arg Tyr Pro Ile Cys Cys Tyr
                85                  90

<210> SEQ ID NO 13
<211> LENGTH: 31
<212> TYPE: PRT
<213> ORGANISM: Homo sapiens

<400> SEQUENCE: 13

Ile Cys His Cys Arg Val Leu Tyr Cys Ile Phe Gly Glu His Leu Gly
1               5                   10                  15

Gly Thr Cys Phe Ile Leu Gly Glu Arg Tyr Pro Ile Cys Cys Tyr
                20                  25                  30
```